US012496100B2

(12) United States Patent
Zhang et al.

(10) Patent No.: US 12,496,100 B2
(45) Date of Patent: Dec. 16, 2025

(54) HINGE-LINK SPINAL CORRECTION DEVICE AND METHOD

(71) Applicant: Texas Scottish Rite Hospital for Children, Dallas, TX (US)

(72) Inventors: Hong Zhang, Irving, TX (US); John David Ross, Jr., Ovilla, TX (US); Daniel J. Sucato, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 391 days.

(21) Appl. No.: 18/152,018

(22) Filed: Jan. 9, 2023

(65) Prior Publication Data

US 2023/0157729 A1 May 25, 2023

Related U.S. Application Data

(63) Continuation-in-part of application No. 16/820,097, filed on Mar. 16, 2020, now Pat. No. 11,596,446.
(Continued)

(51) Int. Cl.
*A61B 17/70* (2006.01)
*A61B 17/88* (2006.01)

(52) U.S. Cl.
CPC ...... *A61B 17/7037* (2013.01); *A61B 17/7008* (2013.01); *A61B 17/7047* (2013.01)

(58) Field of Classification Search
CPC ............ A61B 17/7008; A61B 17/7023; A61B 17/7019; A61B 17/7037; A61B 17/7047;
(Continued)

(56) References Cited

U.S. PATENT DOCUMENTS 5,672,175 A 9/1997 Martin
5,797,910 A 8/1998 Martin
(Continued)

FOREIGN PATENT DOCUMENTS

CN 102499741 B 12/2013
DE 3936702 A1 5/1991
(Continued)

OTHER PUBLICATIONS

International Search Report and Written Opinion for PCT/US2024/057046 by KIPO dated Mar. 14, 2025, 10 pp.
(Continued)

*Primary Examiner* — Eduardo C Robert
*Assistant Examiner* — David C Comstock
(74) *Attorney, Agent, or Firm* — Edwin S. Flores; Daniel J. Chalker; Chalker Flores, LLP

(57) ABSTRACT

A device for spinal correction includes a stabilizer assembly including a hinge including a first rod-bearing leaf; a second rod-bearing leaf rotatably coupled to the first rod-bearing leaf to provide coronal or sagittal freedom of movement, or both, of the stabilizer assembly; a locking mechanism to lock the first and second rod-bearing leaves at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first or second stabilizing rod and is movably couplable to a first spinal rod or a second spinal rod fixed to the spine; wherein the stabilizer assembly is couplable to the first or second spinal rod to stabilize the spine to prevent compression, distraction, or translation of the spinal cord during a spinal correction.

9 Claims, 42 Drawing Sheets

Related U.S. Application Data

(60) Provisional application No. 62/822,345, filed on Mar. 22, 2019.

(58) Field of Classification Search
CPC .............. A61B 17/7049; A61B 17/705; A61B 17/7052
USPC ....... 606/246, 257, 264, 265, 266, 270, 277, 606/279, 90, 105, 86 A
See application file for complete search history.

(56) References Cited

U.S. PATENT DOCUMENTS

| | | | | |
|---|---|---|---|---|
| 6,755,828 | B2 | 6/2004 | Shevtsov et al. | |
| 7,455,685 | B2 | 11/2008 | Justis | |
| 8,016,861 | B2 | 9/2011 | Mitchell et al. | |
| 9,402,660 | B2 | 8/2016 | Brinkman et al. | |
| 9,433,433 | B2 | 9/2016 | Montello et al. | |
| 9,579,126 | B2 | 2/2017 | Zhang et al. | |
| 10,004,538 | B2 | 6/2018 | McNab et al. | |
| 10,105,166 | B2 | 10/2018 | Zhang et al. | |
| 2005/0240181 | A1* | 10/2005 | Boomer | A61B 17/7074 606/280 |
| 2006/0229611 | A1* | 10/2006 | Avery | A61B 17/705 606/279 |
| 2009/0198279 | A1 | 8/2009 | Zhang et al. | |
| 2010/0030273 | A1 | 2/2010 | Mitchell et al. | |
| 2010/0312281 | A1* | 12/2010 | Barry | A61B 17/7077 606/279 |
| 2012/0221057 | A1* | 8/2012 | Zhang | A61B 17/7086 606/279 |
| 2014/0100612 | A1 | 4/2014 | Suddaby | |
| 2014/0249591 | A1 | 9/2014 | Peultier et al. | |
| 2017/0056074 | A1 | 3/2017 | Zhang et al. | |
| 2018/0110506 | A1 | 4/2018 | Thommen et al. | |
| 2018/0280062 | A1* | 10/2018 | Lee | A61B 17/8615 |
| 2021/0186567 | A1 | 6/2021 | Bobbitt et al. | |

FOREIGN PATENT DOCUMENTS

| | | | |
|---|---|---|---|
| WO | 2012074803 | A1 | 6/2012 |
| WO | 2015092270 | A1 | 6/2015 |
| WO | 2020197830 | A1 | 10/2020 |

OTHER PUBLICATIONS

Boachie-Adjei O, et al, "Late treatment of tuberculosis-associated kyphosis: literature review and experience from a SRS-GOP site," Eur Spine J., May 2012, 22 Suppl 4, pp. S641-S646.

Boachie-Adjei O, et al., "Incidence and risk factors for major surgical complications in patients with complex spinal deformity: a report from an SRS GOP site," Spine Deformity, Jun. 2014, 3: 57-64.

Boachie-Adjei O, et al., "The Use of Halo-Gravity Traction and Vertebral Column Resection to Treatc Hildren with Severe Kyphosis. Results and Complications," Ann Pediatr Child Health May 2017, 5(3): 1129, 4 pp.

Boachie-Adjei O, et al., "New neurologic deficit and recovery rates in the treatment of complex pediatric spine deformities exceeding 100 degrees or treated by vertebral col. resection (VCR)," Oct. 2020, Spine Deformity. 9: 427-433.

Boachie-Adjei O, et al., "Surgical outcomes of severe spinal deformities esceeding 100° or treated by vertebral col. resection (VCR). Does implant density matter: an observational study of deformity groupings," Spine Deformity, Mar. 2022, 10: 595-606.

Lenke LG, et al., "Posterior vertebral col. resection for severe pediatric deformity: minimum two-year follow-up of thirty-five consecutive patients," Spine, Mar. 2009, vol. 34:20, pp. 2213-2221.

Lenke LG, et al, "Vertebral Column resection for the treatment of severe spinal deformity," Clin Orthop Relat Res. Sep. 2009, 468: pp. 687-699.

Lenke LG, et al., "Complications after 147 consecutive vertebral column resection for severe pediatric spinal deformity: a multicenter analysis," Spine 2013, vol. 38:2. pp. 119-132.

Miladi L (2013) Round and angular kyphosis in pediatric patients. Orthopaedic & Traumatology: Surgery & Research. Nov. 24, 2012, 99S: S140-S149.

Sacramento-Dominguez C, et al., "Apex of deformity for three-column osteotomy. Does it matter in the occurrence of complications?" The Spine Journal, Jul. 1, 2015, vol. 15, pp. 2351-2359.

Saifi C, et al, "Vertebral column resection for rigid spinal deformity," Global Spine Journal, 2017, vol. 7(3), pp. 280-290.

Sucato DJ, "Management of Severe Spinal Deformity," Spine, 2010, vol. 35:25, pp. 2186-2192.

Suk S, et al., "Posterior vertebral col. resection for severe spinal scoliosis," Spine, 2005 30:14, pp. 1682-1687.

Suk S, et al., "Posterior vertebral col. resection in fixed lumbosacral deformity," Spine, 2005 vol. 30:23, pp. E703-E710.

Suk S, Kim, J-H, et al. "Posterior vertebral column resection for severe spinal deformities," Spine, Jun. 2002, vol. 27:21, pp. 2374-2382.

Syvanen J., et al, "Health-related quality of life after posterior vertebral column resection in children: comparison with healthy controls," European Journal of Orthopaedic Surgery & Traumatology, Jun. 2021, vol. 32, pp. 899-907.

Zhang H and Sucato DJ (2015) Rod link reducer posterior system for vertebral column resection: a porcine model. In: Wang Y, Boachie O, and Lenke L (eds) Spinal Osteotomy. Springer, pp. 163-178.

Zhang H, Sucato DJ, and Ross D, "A novel hinge-link correction system for vertebral col. resection: a pilot study in a porcine model," Spine Deformity, Nov. 2022, vol. 11: 269-279.

International Search Report and Written Opinion for PCT/US2024/037876 by KIPO dated Nov. 6, 2024, 8 pp.

International Search Report and Written Opinion for PCT/US2023/086049 by KIPO dated Apr. 30, 2024, 14 pp.

* cited by examiner

HINGE-LINK SPINAL CORRECTION DEVICE AND METHOD

CROSS-REFERENCE TO RELATED APPLICATIONS

This application is a continuation-in-part patent application of U.S. Ser. No. 16/820,097 filed on Mar. 16, 2020, which is a non-provisional patent application of and claims priority to U.S. provisional patent application Ser. No. 62/822,345 filed on Mar. 22, 2019 and entitled "Hinge-Link Spinal Correction Device and Method," the contents of which are hereby incorporated by reference in their entirety.

STATEMENT OF FEDERALLY FUNDED RESEARCH

Not applicable.

TECHNICAL FIELD OF THE INVENTION

The present invention relates in general to the treatment of spinal deformations. In particular, the present invention relates to the correction of spinal deformation in which a vertebral column resection is performed.

BACKGROUND OF THE INVENTION

Without limiting the scope of the invention, its background is described in connection with the use of a device to stabilize and manipulate a deformed spine on which a vertebral column resection (VCR) or spinal correction is being or has been performed into a desired position and then fixing the spine in that configuration. In some cases of severe spinal deformity, it is advisable to remove one or more vertebrae to allow manipulation of the spine into a more normal curve, sometimes in stages over a period of time. The spine must be stabilized for performance of the VCR; manipulated into the more normal configuration; held in place over a period of time until the spine adapts to that configuration, and sometimes stabilized and manipulated repeatedly during subsequent spinal corrections and then held in place until the spine adapts to each new configuration. Prior art method and systems are difficult and risky because they do not provide for fine control of the initial stabilization during the VCR, stabilization, manipulation, or the long-term fixing in place of the spine without risk of compression, distraction, or translation of the spinal cord.

U.S. Pat. No. 9,433,433, to Montello, et al., is said to disclose a posterior vertebral plating system comprising a plate and a plurality of attachment members. The plate is said to have a plurality of holes extending through the plate from an upper surface to a lower surface, and the plate is configured to extend along the posterior side of at least two vertebrae adjacent at least one boney structure of each of the vertebrae. The holes are said to be spaced in such a way that a first plurality of holes is positionable over a boney structure of a first vertebra to define a plurality of fixation points to the first vertebra and a second plurality of holes is positionable over boney structure of a second vertebra to define a plurality of fixation points to the second vertebra. The attachment members are said to be insertable through the holes of the plate and into the boney structure of a corresponding vertebra to fix the plate to the vertebra.

U.S. Pat. No. 10,004,538, to McNab et al., is said to disclose a surgical instrument that includes a first arm engageable with a first spinal construct disposed with a first vertebral surface. A second arm is said to be connected with the first arm via a pivot and to be engageable with a second spinal construct disposed with a second vertebral surface. The first arm is said to be movable to rotate the first spinal construct relative to the pivot and/or the second arm is said to be movable to rotate the second spinal construct relative to the pivot such that the first vertebral surface is moved relative to the second vertebral surface.

U.S. Pat. No. 9,579,126, to Zhang, et al., and U.S. Pat. No. 10,105,166, to Zhang, et al., are said to disclose a rod link reducer of a spinal fixation system that includes a first and a second spinal rod manipulator; a first spinal rod manipulator joint connected to the first spinal rod manipulator and a second spinal rod manipulator joint connected to the second spinal rod manipulator; a first and a second translatable transverse shaft connected to the first and second joints, respectively; and a universal reducer connected to both the first and second translatable transverse shafts, wherein the universal reducer, the shafts and the linkers provide movement and temporary fixation of a spine that has been manipulated into a final position during spinal surgery.

Methods and systems for stabilization, manipulation, and fixation of a deformed spine subject to a VCR are ineffective and risky. Effective methods and systems that reduce risk for stabilization, manipulation, and fixation of a deformed spine subject to a VCR to prevent compression, distraction, or translation of the spinal cord are desirable.

SUMMARY OF THE INVENTION

In some embodiments of the disclosure, a device for spinal correction is disclosed as including a stabilizer assembly including: a hinge including: a first rod-bearing leaf; a second rod-bearing leaf rotatably coupled to the first rod-bearing leaf to provide coronal or sagittal freedom of movement, or both, of the stabilizer assembly; a locking mechanism to lock the first rod-bearing leaf and the second rod-bearing leaf at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first stabilizing rod or to the second stabilizing rod and is movably couplable to a first spinal rod fixed to a spine or to a second spinal rod fixed to the spine; wherein the stabilizer assembly is couplable to the first spinal rod or to the second spinal rod to stabilize the spine to prevent compression, distraction, or translation of the spinal cord during a spinal correction. In one aspect, the locking mechanism to lock the first rod-bearing leaf and the second rod-bearing leaf at the desired angle includes one or more screws. In another aspect, the first stabilizing rod is coupled to the first rod-bearing leaf with a first threaded portion of the first stabilizing rod. In another aspect, the second stabilizing rod is coupled to the second rod-bearing leaf with a second threaded portion of the second stabilizing rod. In another aspect, each monoaxial or polyaxial link is movably coupled to the first stabilizing rod or to the second stabilizing rod with one or more adjustment nuts or one or more locking pins. In another aspect, each polyaxial link is lockable at a position on the first stabilizing rod or the second stabilizing rod and is lockable at an angle to the first stabilizing rod or the second stabilizing rod with two or more adjustment nuts. In another aspect, each monoaxial or polyaxial link is movably couplable to the first spinal rod or to the second spinal rod at one or more components, each comprising a recess shaped to receive the first spinal rod or to the second spinal rod, and lockable in position with one or more screws. In another aspect, the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and the first stabilizing rod has a locking mechanism to lock it at a desired position or the second stabilizing rod has a locking mechanism to lock it at a desired position. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod.

In some embodiments of the disclosure, a kit is disclosed as including a stabilizer assembly including: a hinge including: a first rod-bearing leaf; a second rod-bearing leaf rotatably coupled to the first rod-bearing leaf to provide coronal or sagittal freedom of movement, or both, of the stabilizer assembly; a locking mechanism to lock the first rod-bearing leaf and the second rod-bearing leaf at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first stabilizing rod or to the second stabilizing rod and is movably couplable to a first spinal rod fixed to a spine or to a second spinal rod fixed to the spine; wherein the stabilizer assembly is couplable to the first spinal rod or to the second spinal rod to stabilize the spine to prevent compression, distraction, or translation of the spinal cord during a spinal correction. In one aspect, the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and the first stabilizing rod has a locking mechanism to lock it at a desired position or the second stabilizing rod has a locking mechanism to lock it at a desired position. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod.

In some embodiments of the disclosure, a method of stabilizing a spine is disclosed as including providing a patient in need of stabilization of a spine, wherein a plurality of spinal rods have been fixed to the spine; coupling a stabilizer assembly of a device for spinal correction to at least one of the plurality of spinal rods, wherein the stabilizer assembly includes: a hinge including: a first rod-bearing leaf; a second rod-bearing leaf rotatably coupled to the first rod-bearing leaf to provide coronal or sagittal freedom of movement, or both, of the stabilizer assembly; and a locking mechanism to lock the first rod-bearing leaf and the second rod-bearing leaf at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first stabilizing rod or to the second stabilizing rod and is movably coupled to a first spinal rod fixed to a spine or to a second spinal rod fixed to the spine; and stabilizing the spine at a desired spinal configuration; wherein the stabilizer assembly is couplable to the first spinal rod or to the second spinal rod to stabilize the spine to prevent compression, distraction, or translation of the spinal cord during a spinal correction. In one aspect, the locking mechanism to lock the first rod-bearing leaf and the second rod-bearing leaf at the desired angle includes one or more screws. In another aspect, the first stabilizing rod is coupled to the first rod-bearing leaf with a first threaded portion of the first stabilizing rod. In another aspect, the second stabilizing rod is coupled to the second rod-bearing leaf with a second threaded portion of the second stabilizing rod. In another aspect, each monoaxial or polyaxial link is movably coupled to the first stabilizing rod or to the second stabilizing rod with one or more adjustment nuts or one or more locking pins. In another aspect, each polyaxial link is lockable at a position on the first stabilizing rod or the second stabilizing rod and is lockable at an angle to the first stabilizing rod or the second stabilizing rod with two or more adjustment nuts. In another aspect, each monoaxial or polyaxial link is movably couplable to the first spinal rod or to the second spinal rod at one or more components, each comprising a recess shaped to receive the first spinal rod or to the second spinal rod, and lockable in position with one or more screws. In another aspect, the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and the first stabilizing rod has a locking mechanism to lock it at a desired position or the second stabilizing rod has a locking mechanism to lock it at a desired position. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod. In another aspect, the method further includes coupling the stabilizer assembly to at least one of the plurality of spinal rods oriented to allow the hinge to have coronal freedom of movement, sagittal freedom of movement, or a combination of coronal and sagittal freedom of movement.

BRIEF DESCRIPTION OF THE DRAWINGS

For a more complete understanding of the features and advantages of the present invention, reference is now made to the detailed description of the invention along with the accompanying figures, in which.

DETAILED DESCRIPTION OF THE INVENTION

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1A:
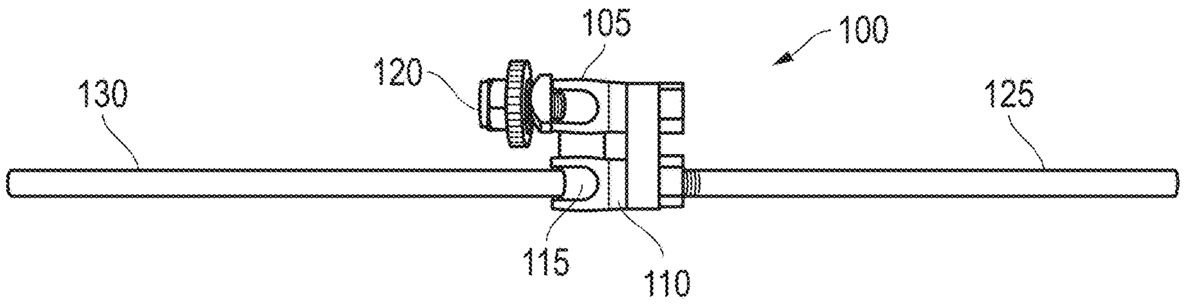
FIGS. 1A, 1B, and 1C show a stabilizer assembly.
Figure 1B:
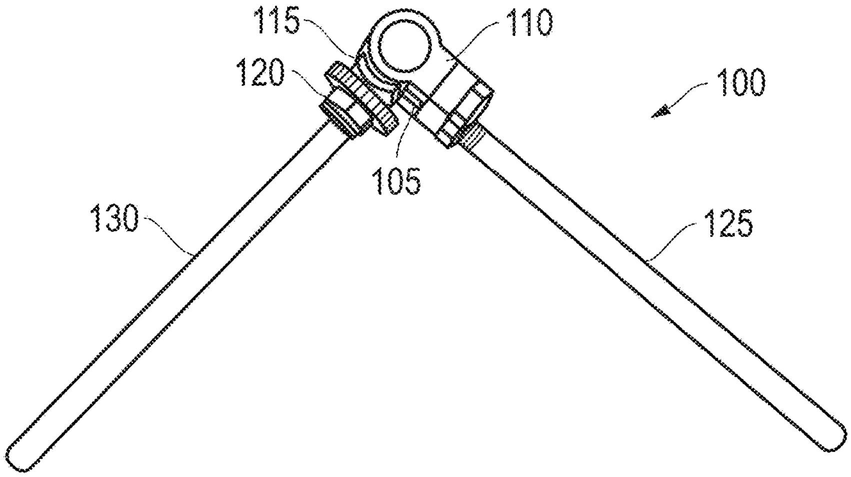

FIGS. 1A and 1B show an embodiment of the present invention which prevents compression, distraction, or translation of the spinal cord during a vertebral resection surgery, the stabilizer assembly 100. FIG. 1A shows a side view and FIG. 1B shows a top view. The stabilizer assembly 100 includes the hinge 105, which includes rod-bearing leaves 110 and 115 and hinge locking mechanism 120. The rod-bearing leaf 115 is rotatably coupled to the rod-bearing leaf 110 to allow coronal or sagittal freedom of movement, or both, depending on the orientation of the stabilizer assembly relative to the spine. Hinge locking mechanism 120 is used to lock the rod-bearing leaves 110 and 115 at a desired angle. Stabilizing rods 125 and 130 are coupled to the rod-bearing leaves 110 and 115, via, e.g., threaded portions of the stabilizing rods 125 and 130 nearest the hinge 105. The stabilizing rod 125, the stabilizing rod 130, or both are threaded and adjustment nuts are mounted on the stabilizing rod 125, the stabilizing rod 130, or both to provide longitudinal freedom of movement.

Figure 1C:
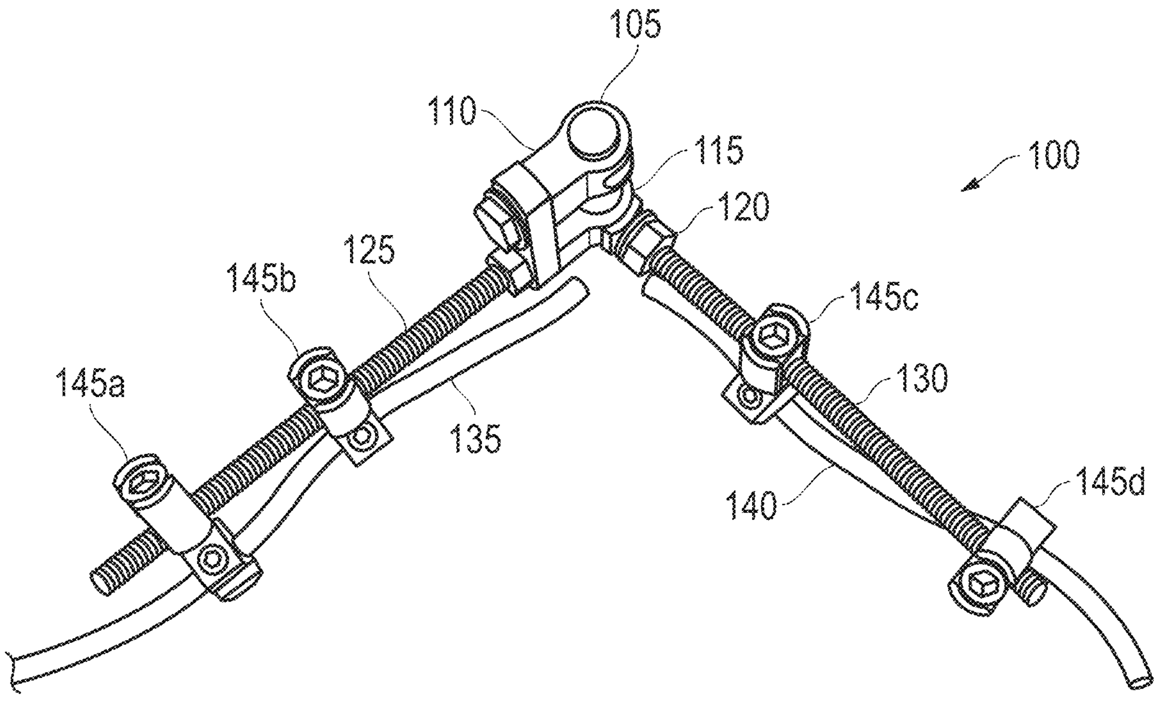

FIG. 1C shows the stabilizer assembly 100 of the present invention coupled to the spinal rods 135 and 140, which may be straight or curved. FIG. 1C shows the hinge 105 with the rod-bearing leaves 110 and 115, the locking mechanism 120, the stabilizing rods 125 and 130, and four links 145*a*, 145*b*, 145*c*, and 145*d*. The links 145*a*, 145*b*, 145*c*, and 145*d* are coupled to the spinal rods 135 and 140. The links 145*a*, 145*b*, 145*c*, and 145*d* represent a number of embodiments of links of the present invention, including monoaxial and polyaxial links described herein.

Figure 2A:
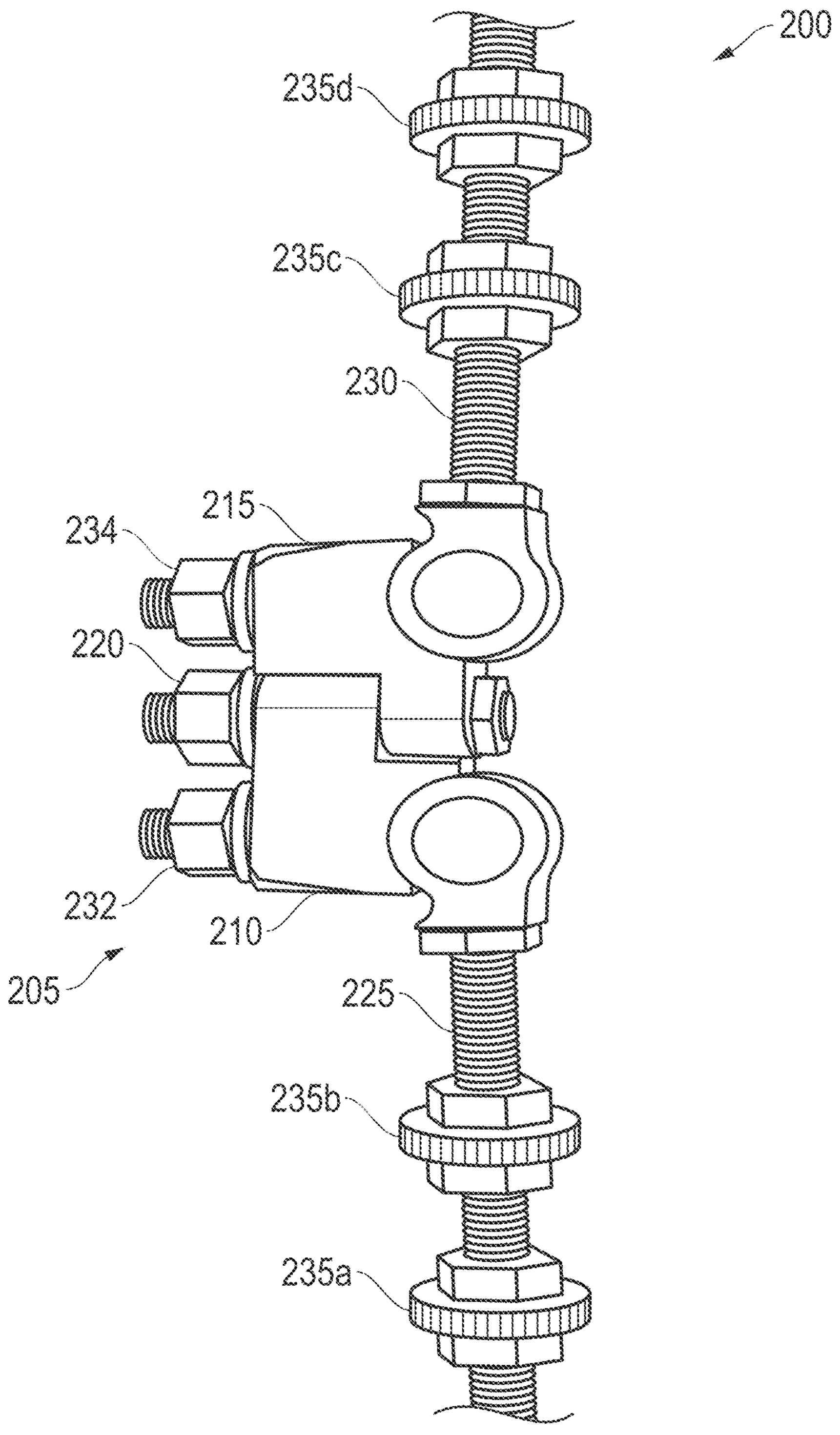
FIG. 2A shows another stabilizer assembly.

FIG. 2A depicts another embodiment of the present invention which prevents compression, distraction, or translation of the spinal cord during a vertebral resection surgery, the stabilizer assembly 200. The stabilizer assembly includes the hinge 205, which is configured to allow coronal or sagittal freedom of movement, or both, of the stabilizer assembly, depending on the orientation of the stabilizer assembly relative to the spine. Rod-bearing leaves 210 and 215 are rotatably coupled to allow coronal or sagittal freedom of movement, or both, depending on the orientation of the stabilizer assembly relative to the spine. Hinge locking mechanism 220 is used to lock the rod-bearing leaves 210 and 215 at a desired angle. Stabilizing rods 225 and 230, which are threaded on at least a portion of their respective lengths, are coupled to the rod-bearing leaves 210 and 215, via, e.g., threaded portions at the ends of the stabilizing rods 225 and 230 nearest the hinge 205. The stabilizing rods 225 and 230 are rotatably coupled to the rod-bearing leaves 210 and 215 such that they have freedom of movement with axes of rotation that are at right angles to a plane formed when the rod-bearing leaves 210 and 215 form a 180-degree angle. Locking mechanisms 232 and 234 are used to lock the stabilizing rods 225 and 230, respectively, at desired positions. The stabilizing rods 225 and 230 are threaded and carry exemplary adjustment nuts 235*a*, 235*b*, 235*c*, and 235*d* to move links (not shown) longitudinally on the stabilizing rods 225 and 230, allowing longitudinal freedom of movement along the stabilizing rods 225 and 230. The adjustment nuts 235*a*, 235*b*, 235*c*, and 235*d* can be used to lock links in place on the stabilizing rods 225 and 230.

Figure 2B:
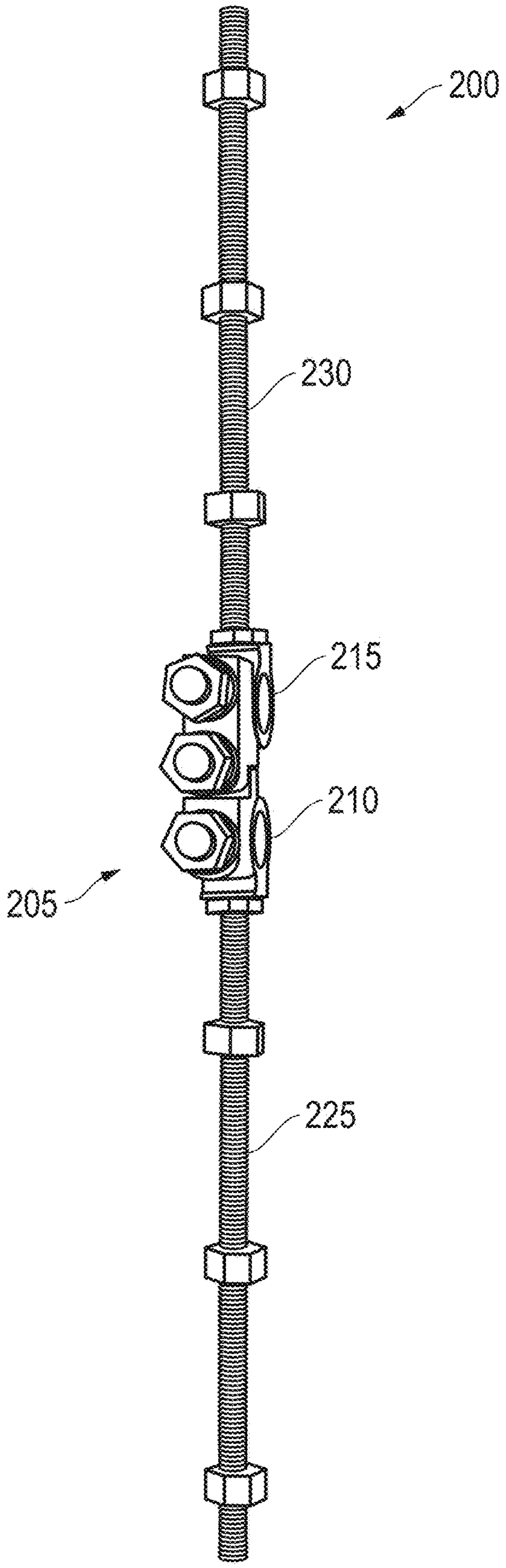
FIGS. 2B, 2C, and 2D illustrate top views of the stabilizer assembly of FIG. 2A.
Figure 2C:
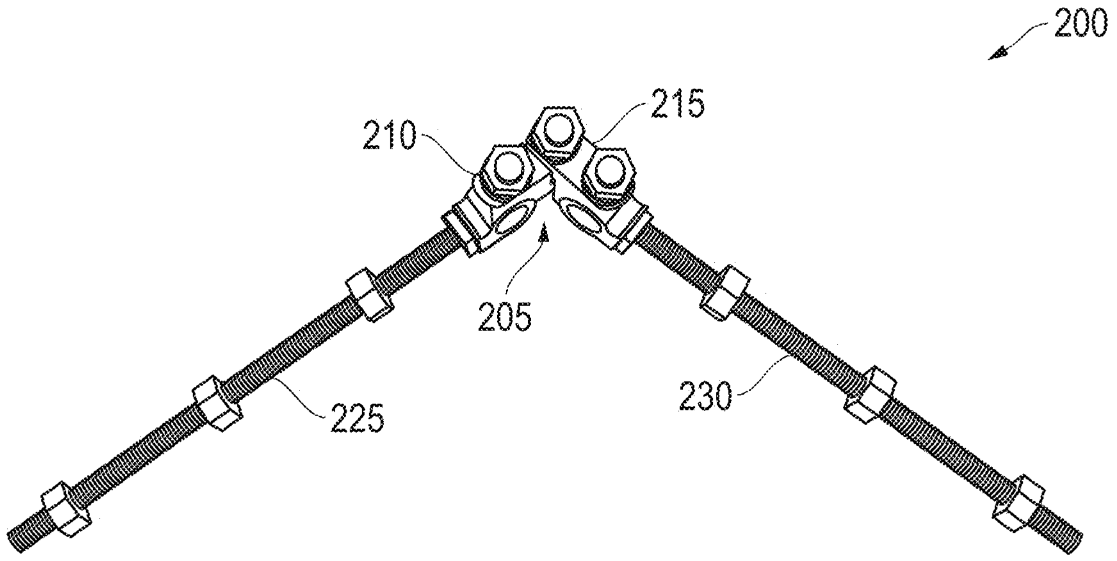
Figure 2D:
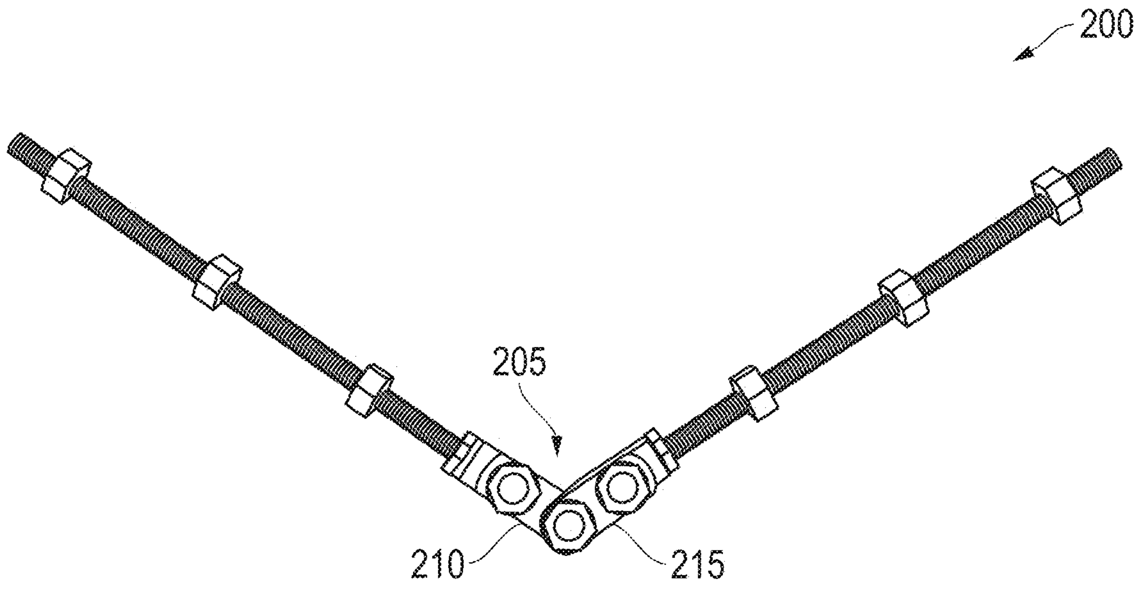

FIG. 2B shows a top view of the stabilizer assembly 200 with the rod-bearing leaves 210 and 215 of the hinge 205 set at a 180-degree angle. FIGS. 2C and 2D depict top views of the stabilizer assembly 200 with the rod-bearing leaves 210 and 215 of the hinge 205 set at different angles to provide examples of the coronal freedom of motion allowed by the hinge 205.

Figure 2E:
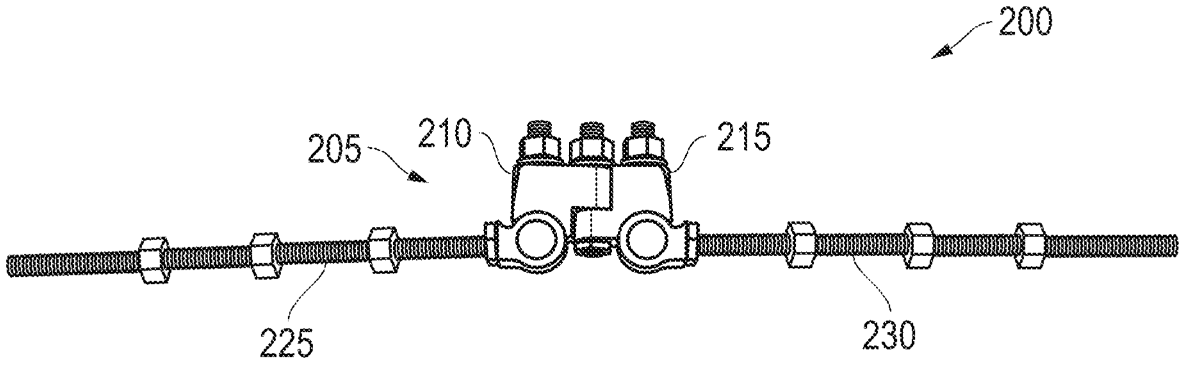
FIGS. 2E, 2F, and 2G illustrate perspective views of the stabilizer assembly of FIG. 2A.
Figure 2F:
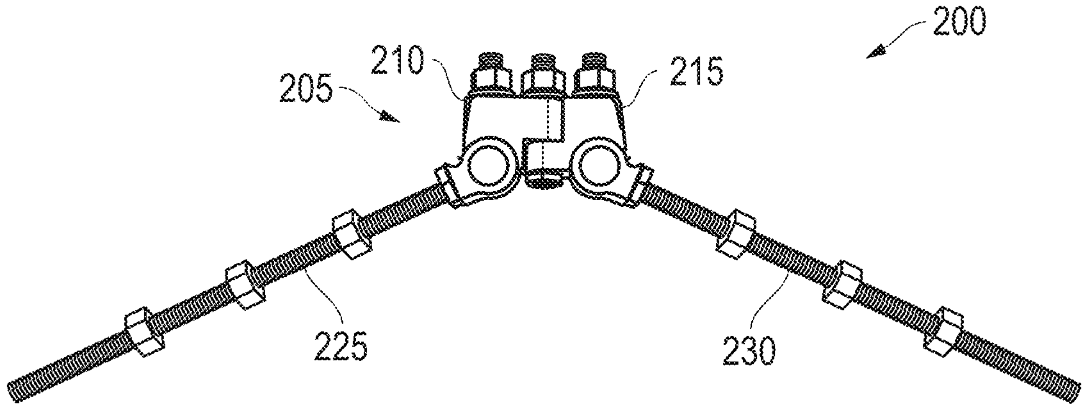
Figure 2G:
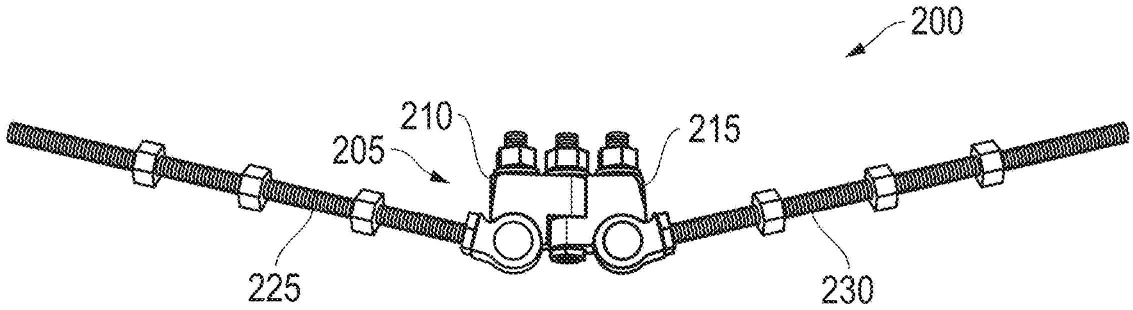

FIG. 2E shows a lateral view of the stabilizer assembly 200 with the rod-bearing leaves 210 and 215 of the hinge 205 set at a 180-degree angle and the stabilizing rods 225 and 230 aligned with each other. FIGS. 2F and 2G depict lateral views of the stabilizer assembly 200 with the rod-bearing leaves 210 and 215 of the hinge 205 set a 180-degree angle and the stabilizing rods 225 and 230 set at different angles to provide examples of the sagittal freedom of motion of the stabilizing rods 225 and 230.

Figure 2H:
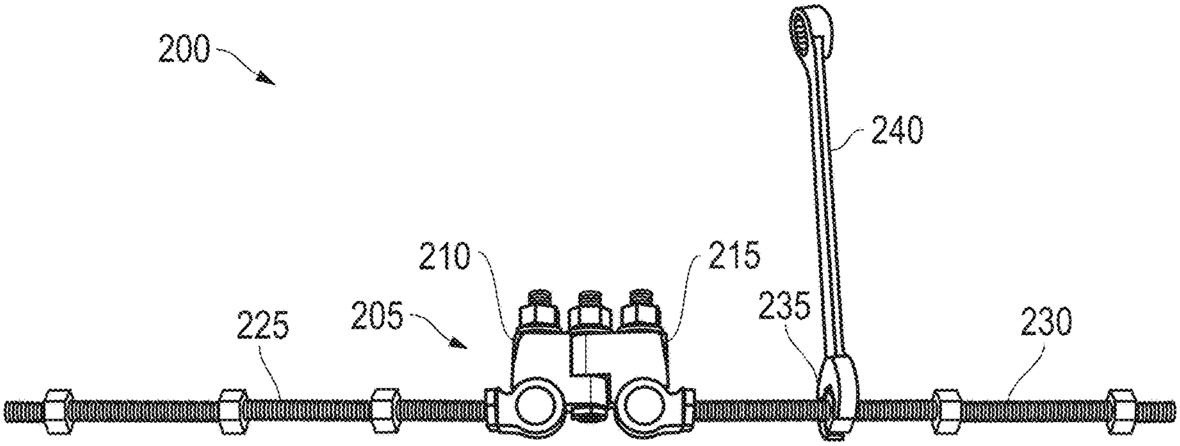
FIG. 2H depicts a view of the stabilizer assembly of FIG. 2A with a wrench to adjust adjustment nuts.

FIG. 2H shows a lateral view of the stabilizer assembly 200 with the rod-bearing leaves 210 and 215 of the hinge 205 set at a 180-degree angle and the stabilizing rods 225 and 230 aligned with each other, with a wrench 240 positioned to adjust an adjustment nut 235 to move it longitudinally on the stabilizing rod 230 to position a link (not shown) on the stabilizing rod 230.

Figure 2I:
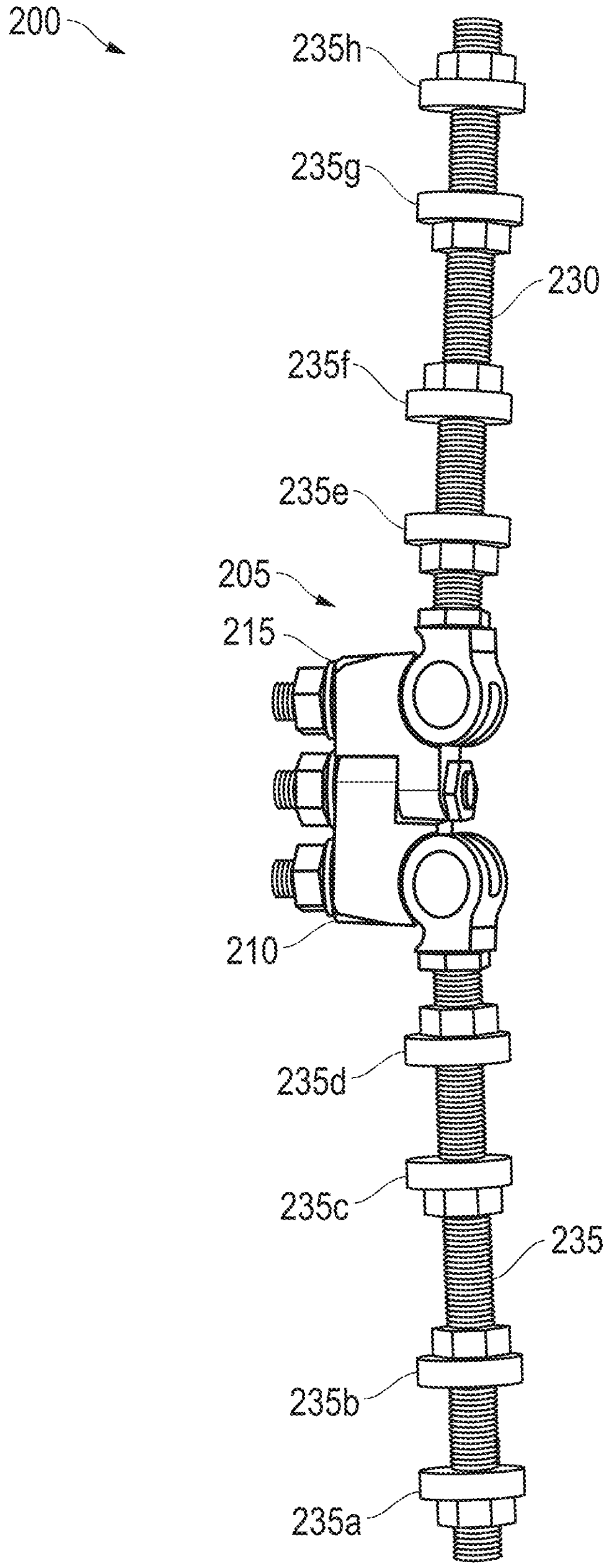
FIG. 2I shows a lateral view of the stabilizer assembly of FIG. 2A.

FIG. 2I shows a lateral view of the stabilizer assembly 200 with the rod-bearing leaves 210 and 215 of the hinge 205 set at a 180-degree angle and the stabilizing rods 225 and 230 aligned with each other, with eight exemplary adjustment nuts 235*a*, 235*b*, 235*c*, 235*d*, 235*e*, 235*f*, 235*g*, and 235*h*, four on each of the stabilizing rods 225 and 230. The adjustment nuts can be made from any material such as metal, polymers, composites, etc.

Figure 3A:
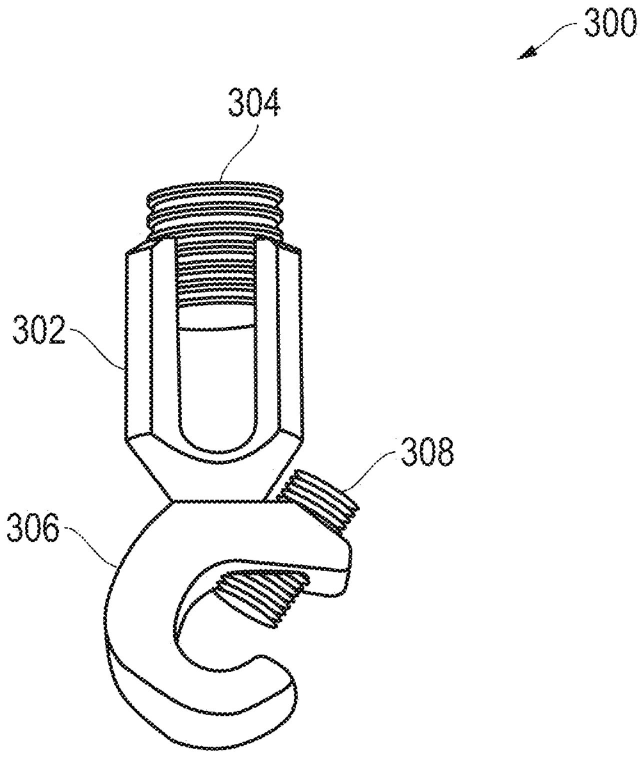
FIG. 3A shows a monoaxial link.

FIG. 3A shows a monoaxial link 300 of the present invention. FIG. 3A illustrates a monoaxial link 300 of the present invention. A plurality of links 300 may be movably coupled to one or both of the stabilizing rods 125 and 130 (not shown), at the upper end 302 of each link 300. Each link 300 can be positioned as desired on a stabilizing rod 125 or 130 using, e.g, a set-screw 304, to lock it into position. Each link 300 is movably couplable to a spinal rod (not shown) that is fixed to a spine using, e.g., bone screws, at the lower end 306 of each link 300. Each link 300 can be positioned as desired on spinal rod using, e.g, a set-screw 308, to lock it into position.

Figure 3B:
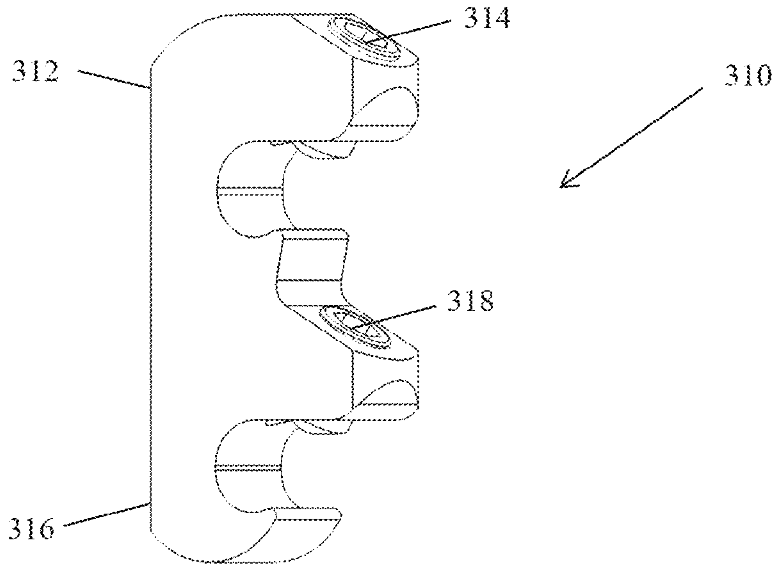
FIG. 3B shows another monoaxial link.

FIG. 3B illustrates another monoaxial link 310 of the present invention. A plurality of links 310 may be movably coupled to one or both of the stabilizing rods 125 and 130 (not shown), at the upper end 312 of each link 310. Each link 310 can be positioned as desired on a stabilizing rod 125 or 130 using, e.g, a set-screw 314, to lock it into position. Each link 310 is movably couplable to a spinal rod (not shown) that is fixed to a spine using, e.g., bone screws, at the lower end 316 of each link 310. Each link 310 can be positioned as desired on spinal rod using, e.g, a set-screw 318, to lock it into position.

Figure 3C:
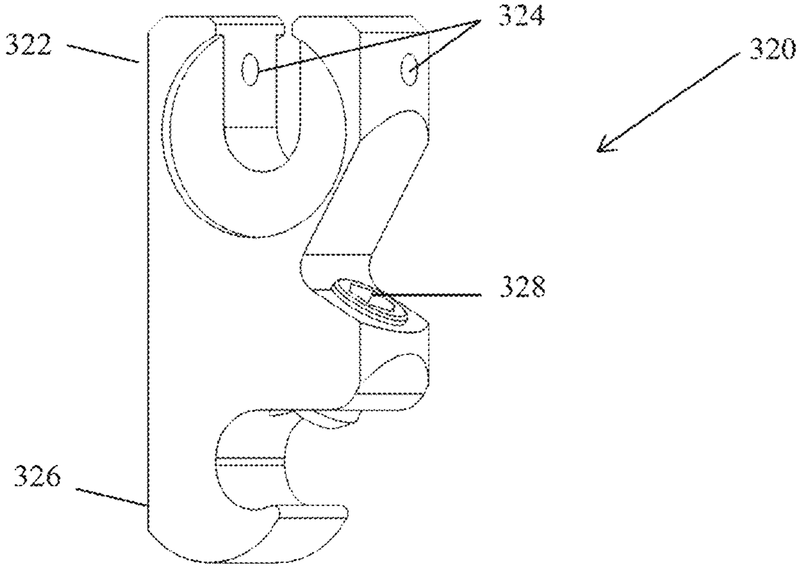
FIG. 3C shows still another monoaxial link.

FIG. 3C illustrates still another monoaxial link 320 of the present invention. A plurality of links 320 may be movably coupled to one or both of the stabilizing rods 125 and 130 (not shown), at the upper end 322 of each link 320. Each link 320 can be positioned as desired on a stabilizing rod 125 or 130 using, e.g, a locking pin (not shown) set in place through holes 324, to retain the link 320 on the stabilizing rod 125 or 130 (not shown). Each link 320 is movably couplable to a spinal rod (not shown) that is fixed to a spine using, e.g., bone screws, at the lower end 326 of each link 320. Each link 320 can be positioned as desired on spinal rod using, e.g, a set-screw 328, to lock it into position.

Figure 3D:
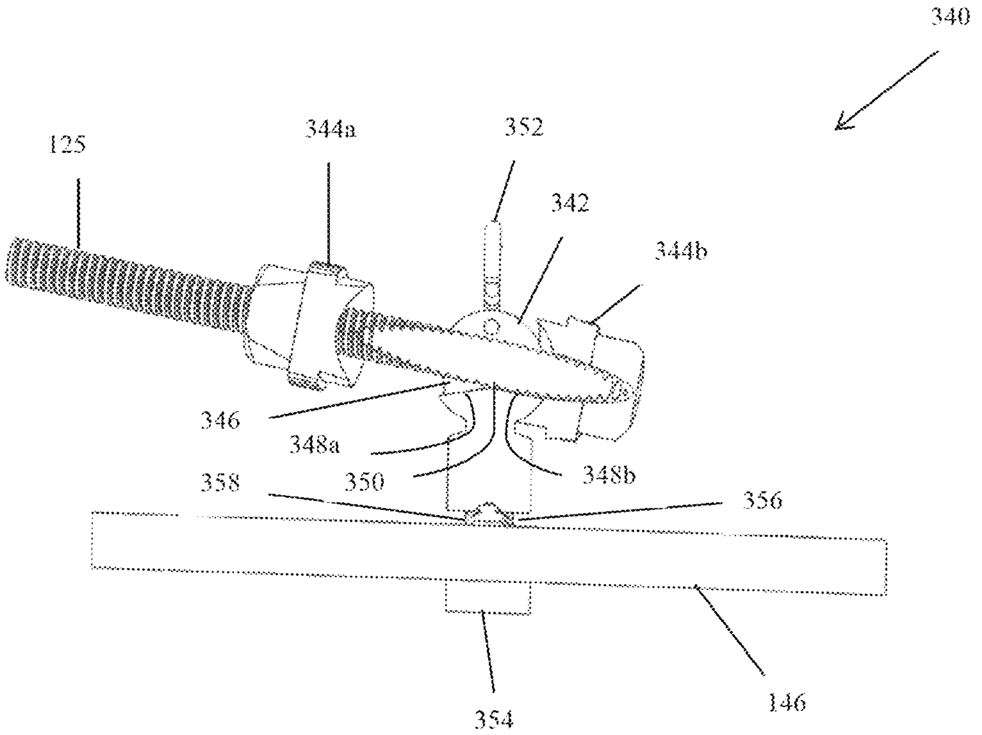
FIG. 3D shows a cross-section of a polyaxial link.

FIG. 3D shows a cross-section, and FIGS. 3E, 3F, 3G, and 3H show perspective views of a polyaxial link 340 of the present invention, with each figure showing one or more features of the polyaxial link 340 in various configurations. Each of a plurality of polyaxial links 340 is movably coupled to one of the stabilizing rods 125 and 130 (of which stabilizing rod 125 is shown and stabilizing rod 130 is not shown), at the upper portion 342 of each polyaxial link 340. Each polyaxial link 340 can be positioned as desired on a stabilizing rod 125 or 130 (130 not shown) using e.g., a pair of adjustment nuts 344*a* and 344*b*, shaped to match the shape of the upper portion 342, to lock it into position. These adjustment nuts 344*a* and 344*b*, and similar ones elsewhere on the threaded stabilizing rod 125 or 130 (130 not shown), can be locked and unlocked multiple times without damaging the adjustment nut threads or the stabilizing rod threads. The upper portion 342 of polyaxial link 340 is spherically shaped with a recess 346 shaped to receive a stabilizing rod 125 or 130 (130 not shown). The recess 346 is wider than the stabilizing rod 125 or 130 (130 not shown), and the bottom of the recess 346 includes two ramped portions 348*a* and 348*b* meeting at an apex 350. When the polyaxial link 340 is positioned on a stabilizing rod 125 or 130 (130 not shown), the stabilizing rod 125 or 130 (130 not shown) contacts at least the apex 350, which keeps the stabilizing rod 125 or 130 (130 not shown) centered in the recess 346, while the width of the recess 346 and the ramps 348*a* and 348*b* permit the polyaxial link 340 to be set at an angle to an axis of the stabilizing rod 125 or 130 (130 not shown) up a limit of, e.g., 10, 15, 20, 25, 30, 35, 40, 45, or more degrees, in any direction. When the stabilizing rod 125 or 130 (130 not shown) is at the desired angle in the recess 346 and the polyaxial link 340 is at the desired position on the stabilizing rod 125 or 130 (130 not shown), the adjustment nuts 344*a* and 344*b* can be used to lock the polyaxial link 340 in place. A locking pin 352 may also be used to further secure the stabilizing rod 125 or 130 (130 not shown) in place. The lower portion 354 of the polyaxial link 340 has a recess 356 shaped to receive a spinal rod 146, which is attached to the patient's spine (not shown). Each polyaxial link 340 can be positioned at a desired location on the spinal rod 146 and locked into place using, e.g, a set screw 358.

Figure 3E:
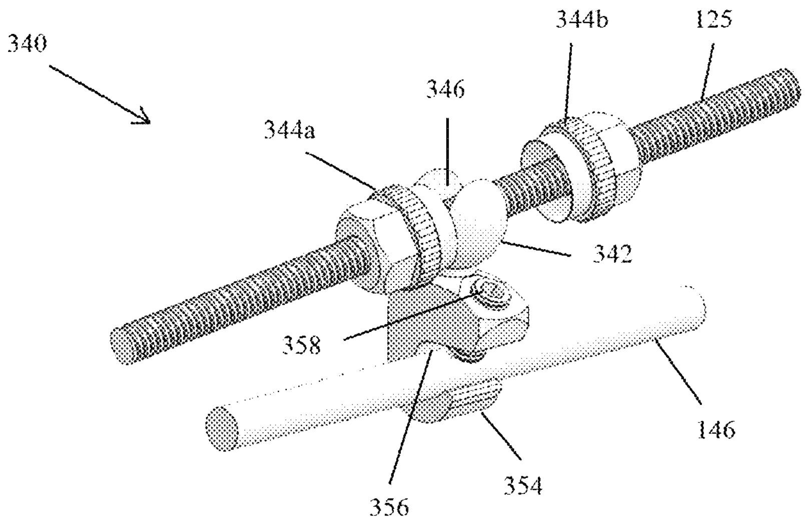
FIGS. 3E, 3F, 3G, and 3H show perspective views of the polyaxial link of FIG. 3D.
Figure 3F:
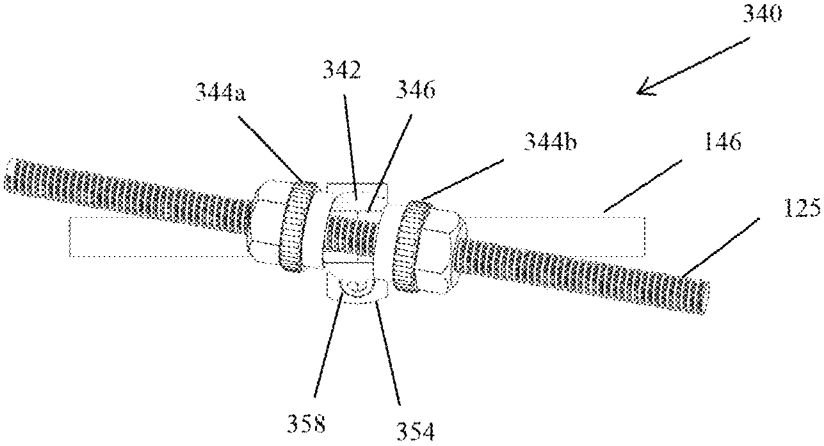
Figure 3G:
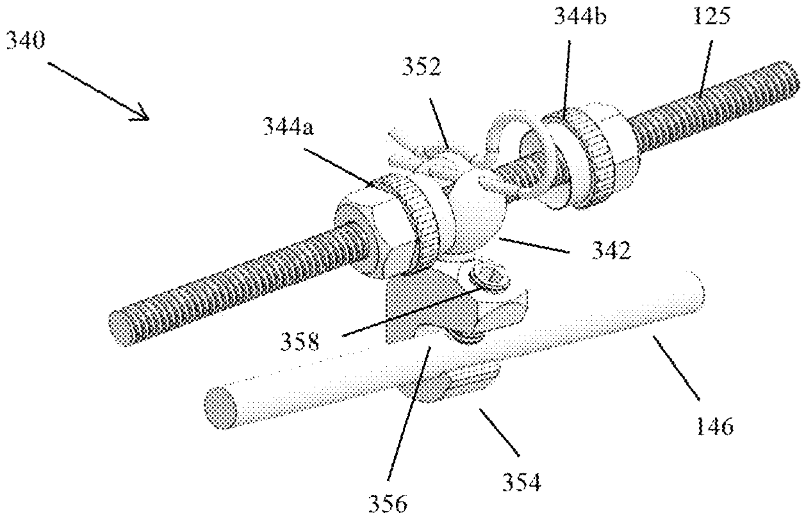
Figure 3H:
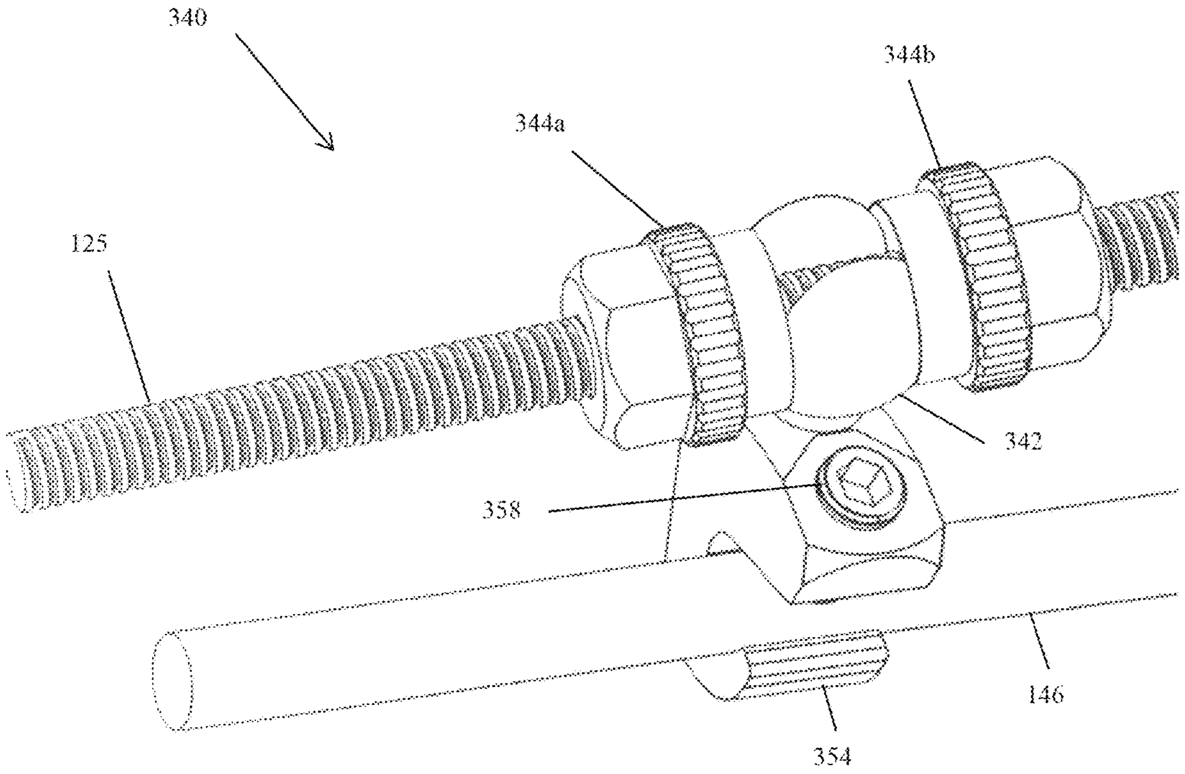

FIG. 3E illustrates the polyaxial link 340 with the adjustment nuts 344*a*, 344*b* disengaged. FIG. 3F shows the polyaxial link 340 from the top, with adjustment nuts 344*a* and 344*b* engaged, and locked into a position at an angle to the stabilizing rod 125. FIG. 3G illustrates the polyaxial link 340 with the adjustment nut 344*a* engaged and adjustment nut 344*b* disengaged and a locking pin 352 in place. FIG. 3H illustrates the polyaxial link 340 with the adjustment nuts 344*a*, 344*b* engaged.

Figure 3I:
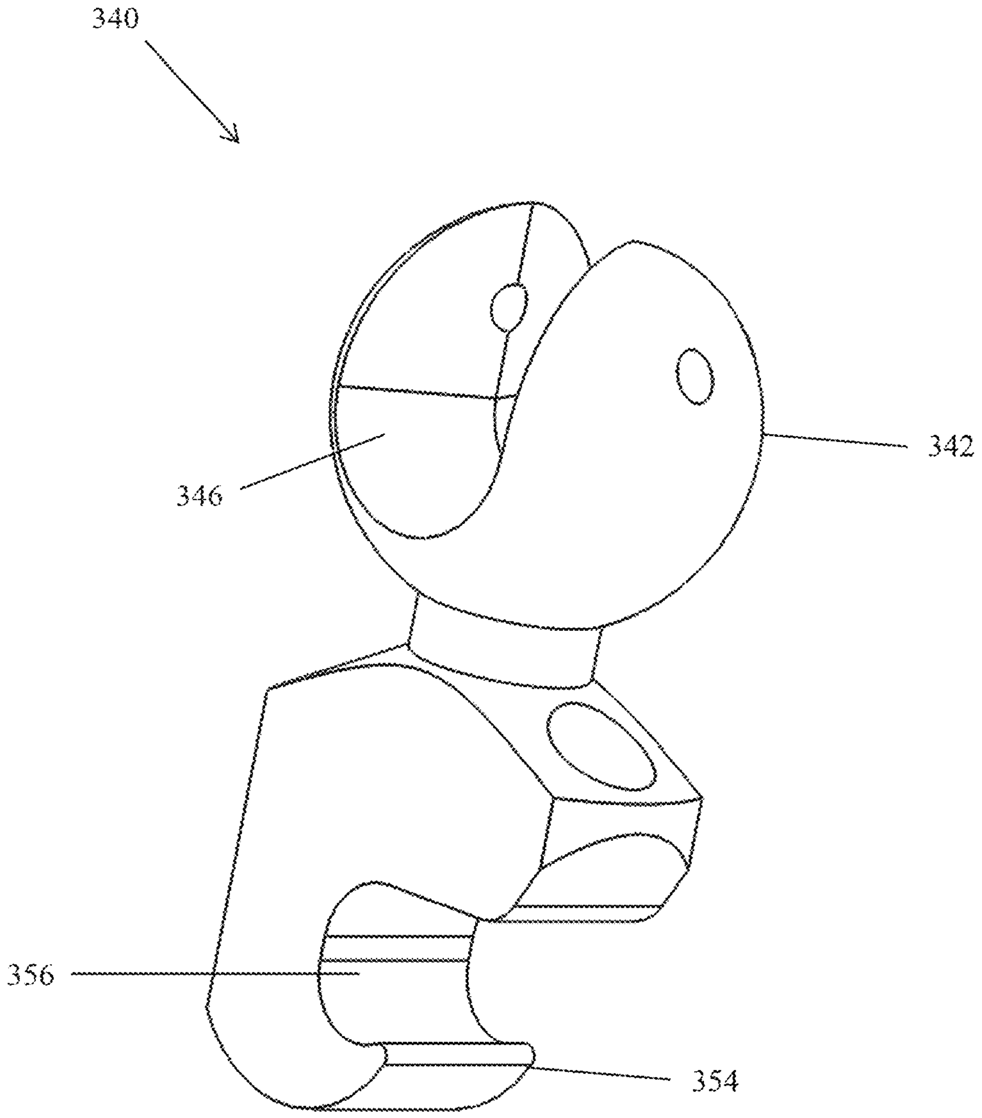
FIG. 3I shows a perspective view of another polyaxial link.

FIG. 3I shows a perspective view of the polyaxial link 340, showing the upper section 342, the recess 346, the lower portion 354, and the recess 356.

Figure 3J:
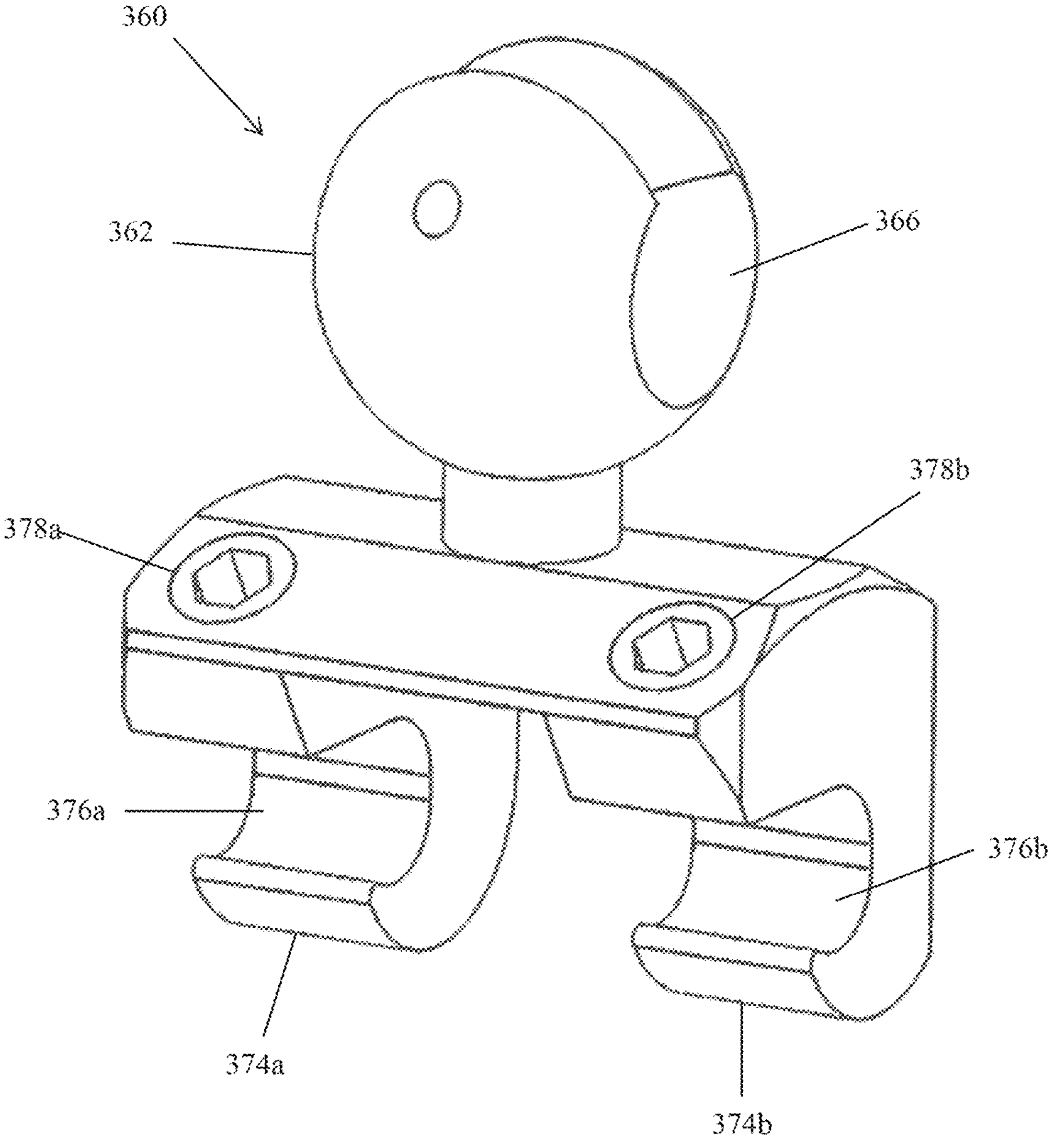
FIG. 3J shows a perspective view of still another polyaxial link.

FIG. 3J shows a perspective view of the polyaxial link 360. The polyaxial link 360 is similar to the polyaxial link 340 except that the bottom end 374 of the polyaxial link 360 has two components or prongs, 374*a* and 374*b*. The prongs 374*a* and 374*b* have recesses 376*a* and 376*b*, respectively, shaped to receive spinal rod 146 (not shown), permitting engagement with a spinal rod 146 at two places. The polyaxial link 360 can be locked into place on spinal rod 146 using screws 378*a* and 378*b*. Engagement of the polyaxial link 360 with spinal rod 146 at two places provides increased stability of the polyaxial link 360 when engaged, compared to single-component or -prong polyaxial links such as the polyaxial link 340. Among other features of the polyaxial link 360, FIG. 3J shows the upper portion 362 of the polyaxial link 360, with a recess 366 shaped to receive stabilizing rod 125 or 130 (neither are shown). The components or prong similar to prongs 374*a* and 374*b* may also be used on the monoaxial links disclosed herein.

Figure 4A:
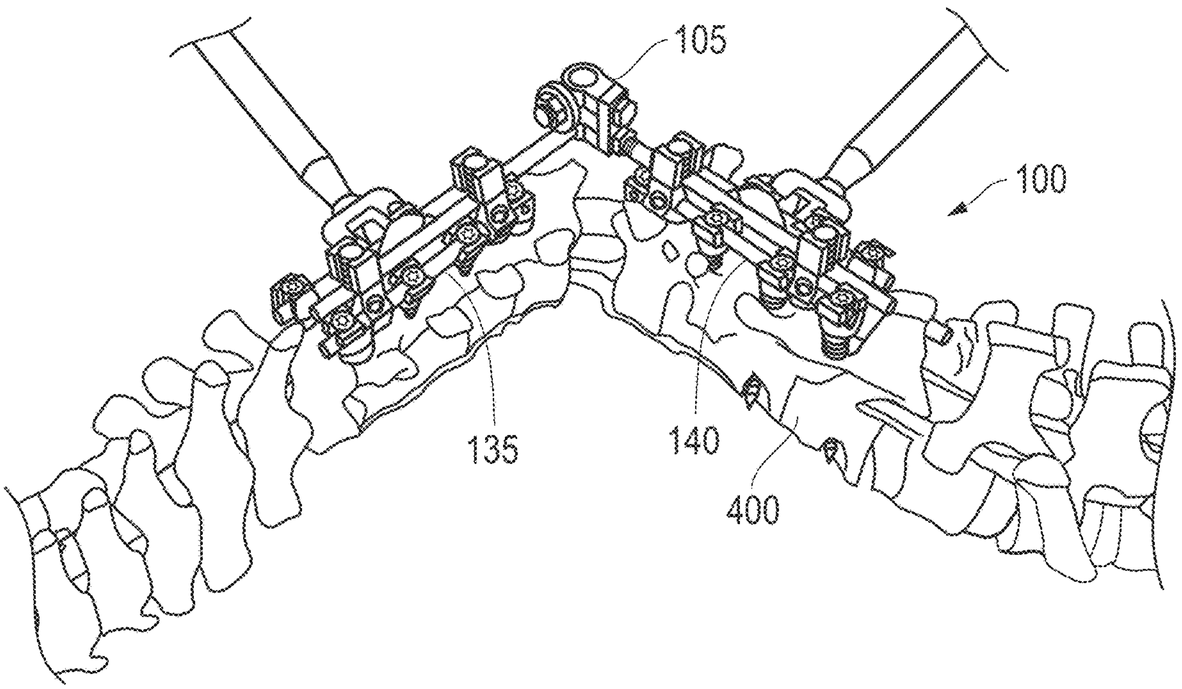
FIGS. 4A, 4B, and 4C illustrate the stabilizer assembly of FIGS. 1A, 1B, and 1C coupled to spinal rods, with the spinal rods attached to a simulated spine.
Figure 4B:
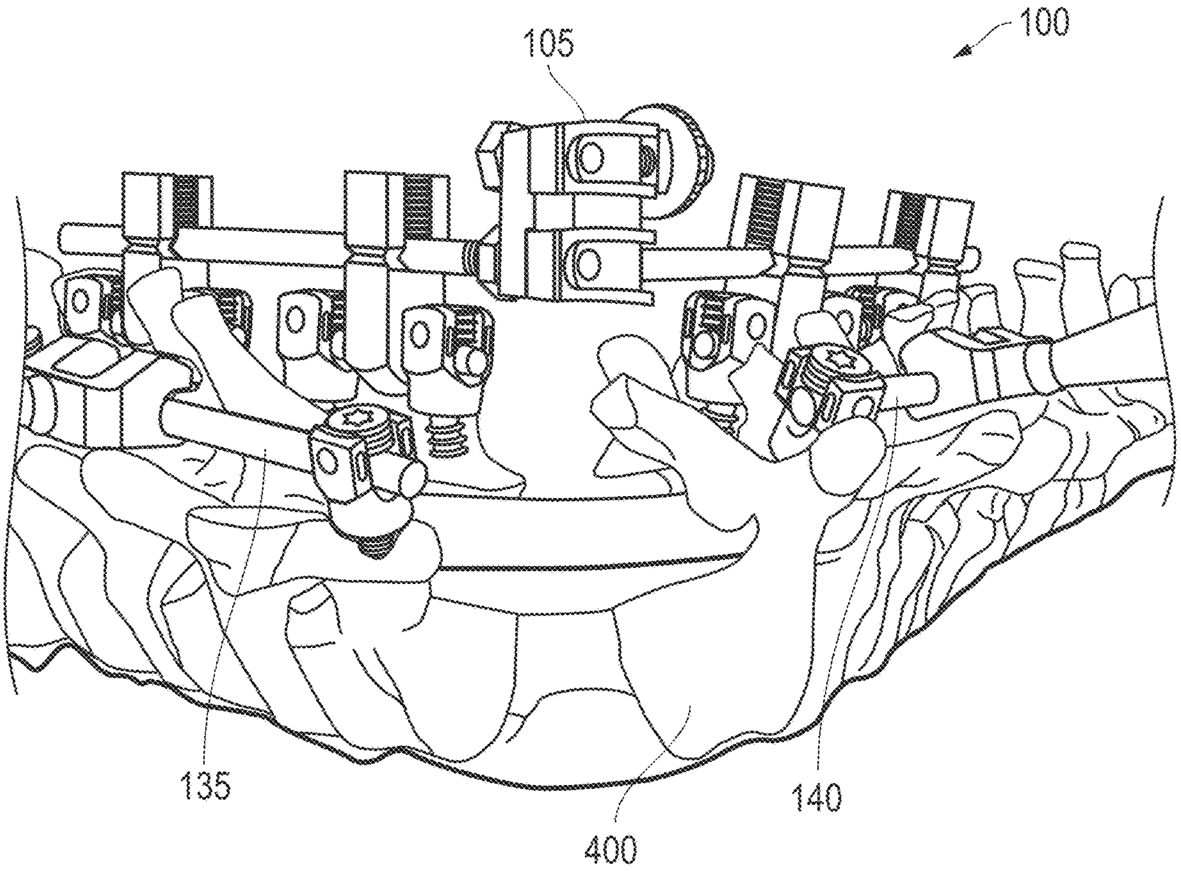
Figure 4C:
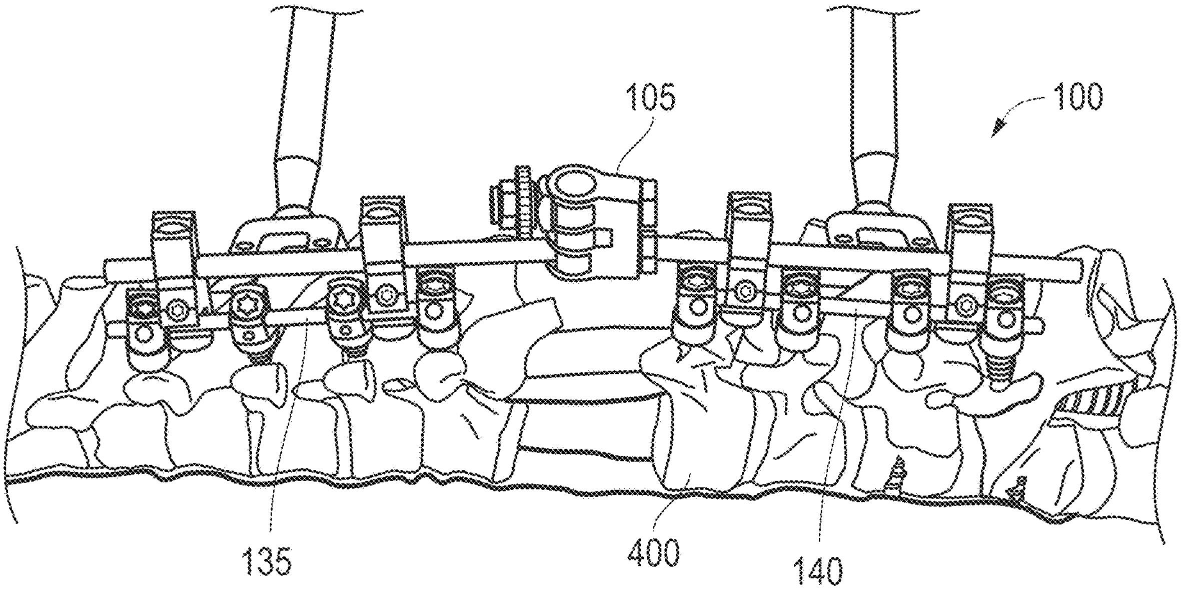

FIGS. 4A, 4B, and 4C illustrate the stabilizer assembly 100 of the present invention coupled to the spinal rods 135 and 140, with the spinal rods 135 and 140 attached to a simulated spine 400. FIGS. 4A and 4B illustrate the hinge 105 positioned at the apex of the spinal deformity, at which a VCR has been performed. FIG. 4C illustrate the hinge 105 positioned at the apex of the spinal deformity, at which the deformity has been corrected.

Figure 5A:
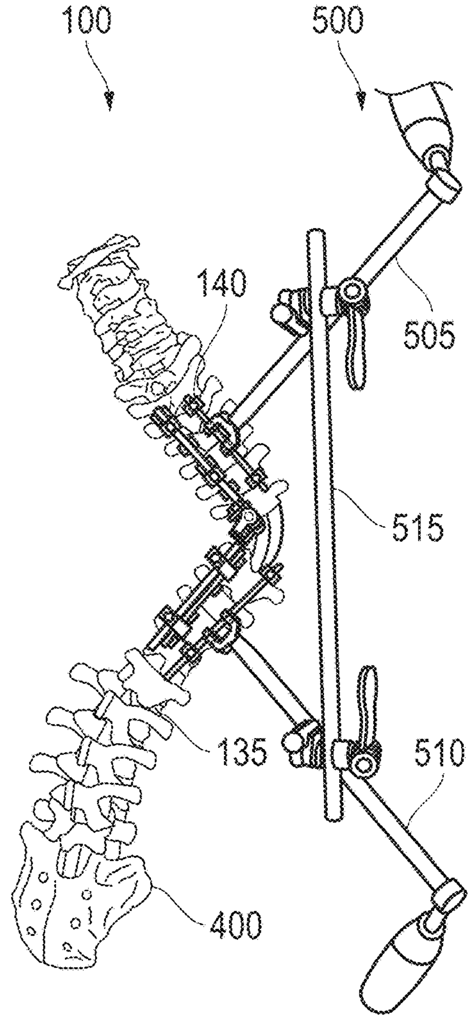
FIGS. 5A and 5B depicts the stabilizer assembly of FIGS. 1A, 1B, and 1C being used with a manipulator assembly.
Figure 5B:
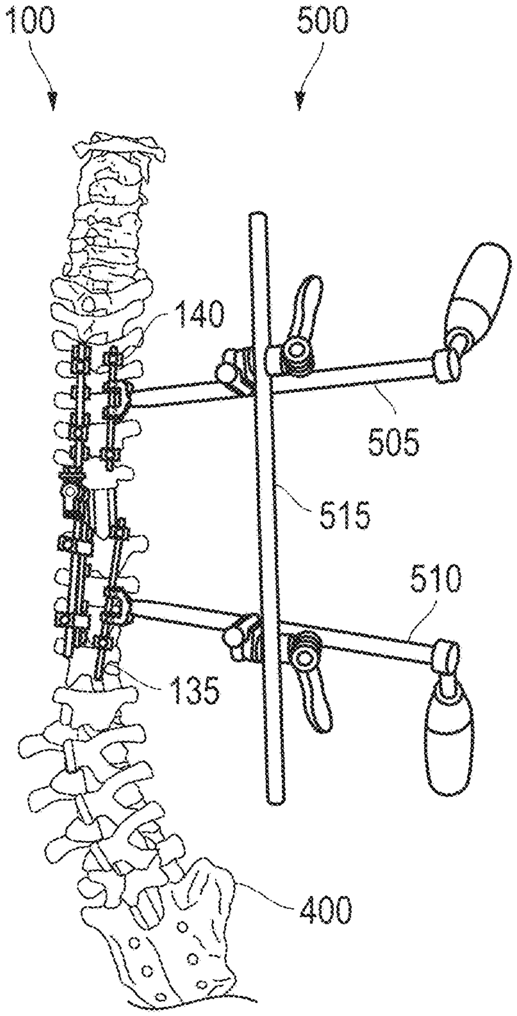

FIGS. 5A and 5B depict the stabilizer assembly 100 being used in conjunction with a manipulator assembly 500. FIGS. 5A and 5B illustrate how the stabilizer assembly 100 and the manipulator assembly 500 are used together to perform a spinal correction. Manipulator assembly 500 includes the handles 505 and 510 and the connecting rod 515. The connecting rod 515 is movably coupled by, e.g., one or more clamps or one or more screws, to the handles 505 and 510 to stabilize or fix the handles 505 and 510 relative to one another as desired. The handles 505 and 510 are couplable to spinal rods 135 and 140 to permit manipulation of the spine into a fixed configuration for the stabilizer assembly to maintain. FIGS. 5A and 5B show the manipulator assembly 500 coupled to two spinal rods 135 and 140, with the handles 505 and 510 in different relative positions and with the simulated spine 400 manipulated to two different desired configurations. The stabilizer assembly 100 is also shown.

Figure 6A:
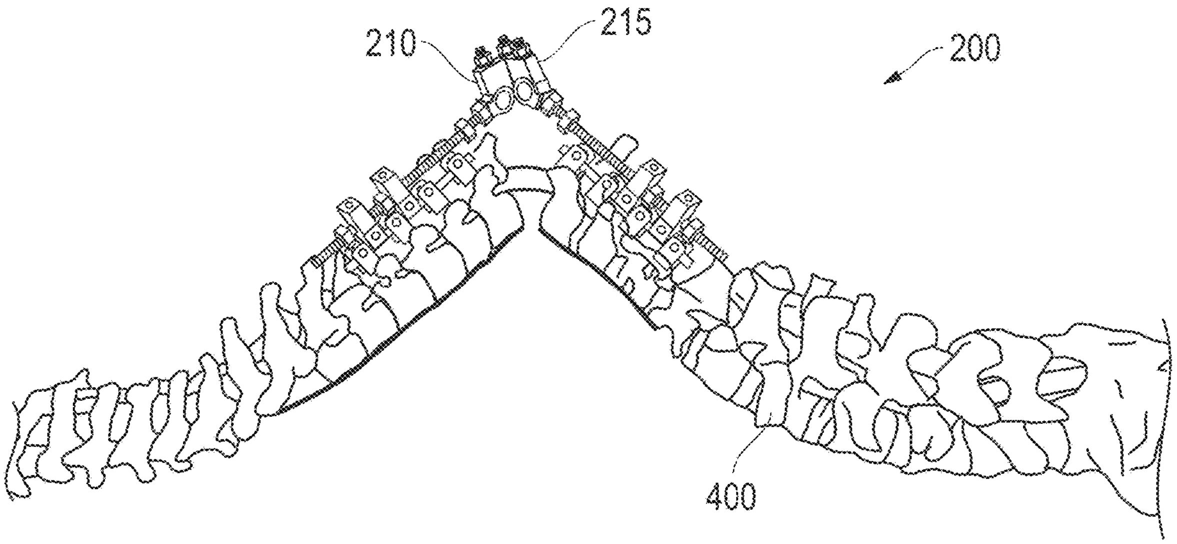
FIGS. 6A, 6B, and 6C show a coronal plane control correction, a sagittal plane control correction, and a longitudinal correction using the stabilizer assembly of FIG. 2A, respectively.
Figure 6B:
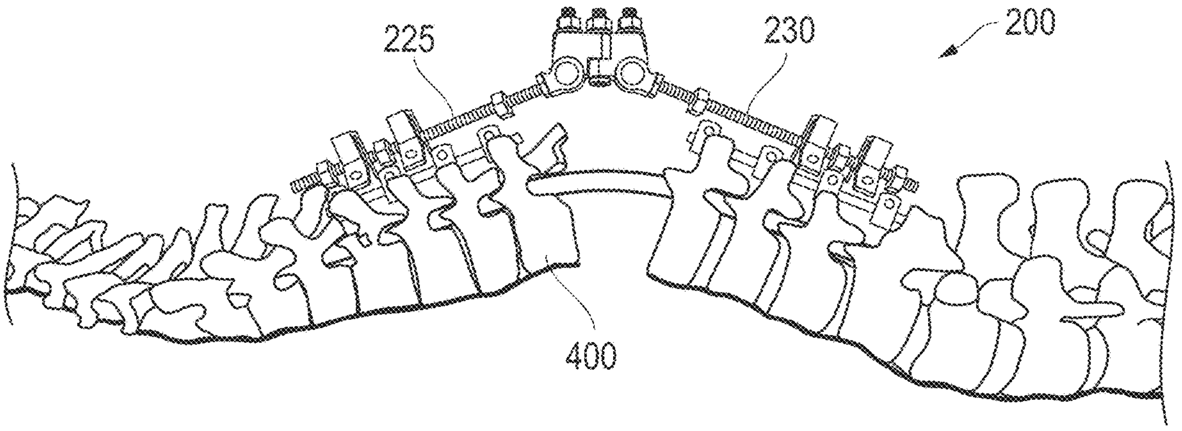
Figure 6C:
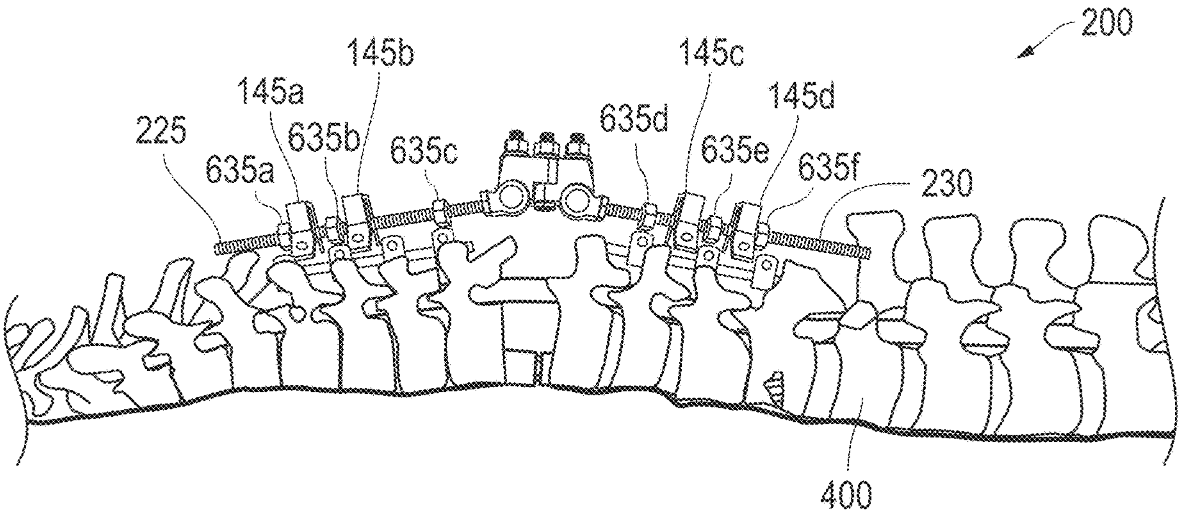

FIG. 6A depicts a coronal plane control correction using the stabilizer assembly 200. The rod-bearing leaves 210 and 215 are set at a desired angle to position the simulated spine 400 as desired. FIG. 6B depicts a sagittal plane control correction using the stabilizer assembly 200. The stabilizing rods 225 and 230 are set at desired positions to position the simulated spine 400 as desired. FIG. 6C depicts a longitudinal correction using the stabilizer assembly 200. The links 145*a*, 145*b*, 145*c*, and 145*d* are set at desired positions by the adjustment nuts 635*a*, 635*b*, 635*c*, 635*d*, 635*e*, and 635*f*.

Figure 6D:
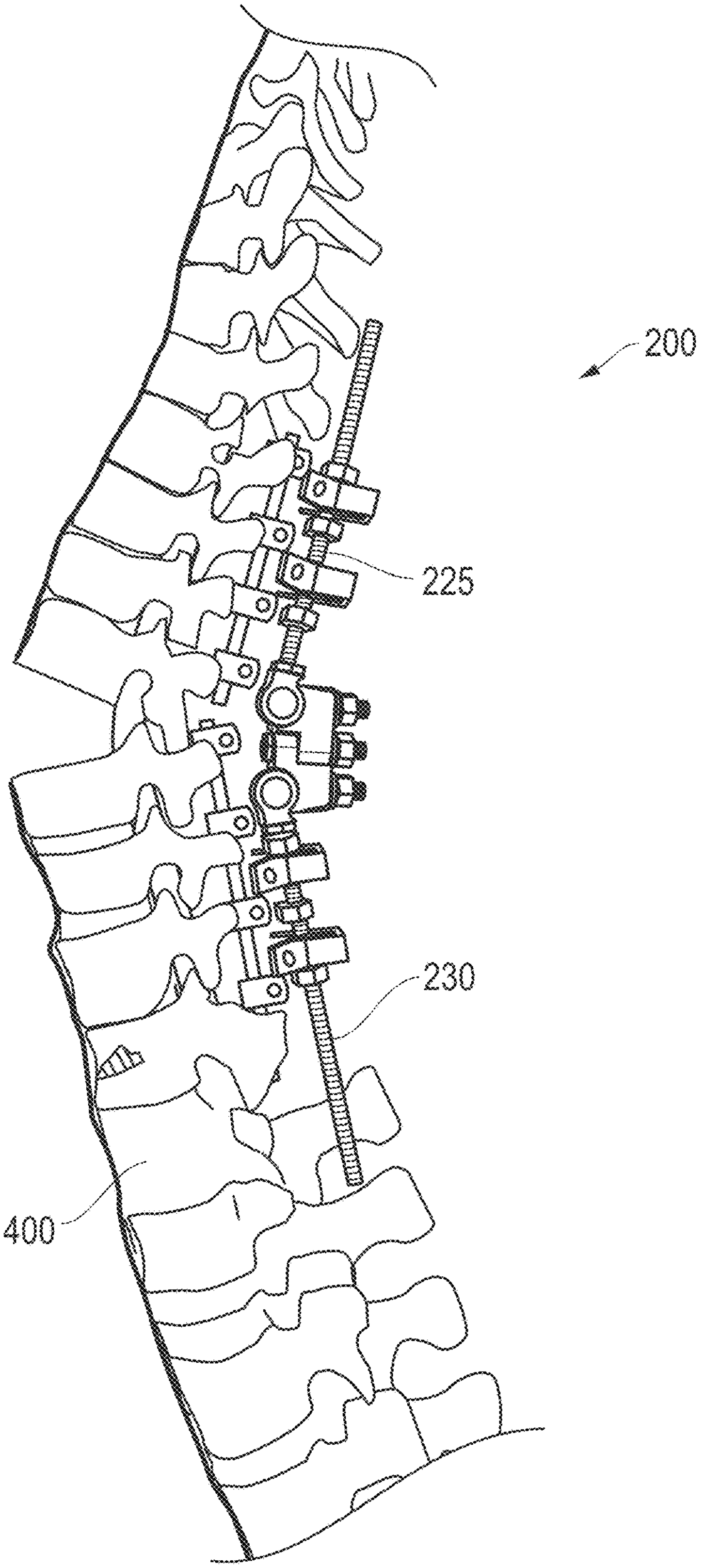
FIGS. 6D and 6E show two different sagittal plane control corrections using the stabilizer assembly of FIG. 2A.
Figure 6E:
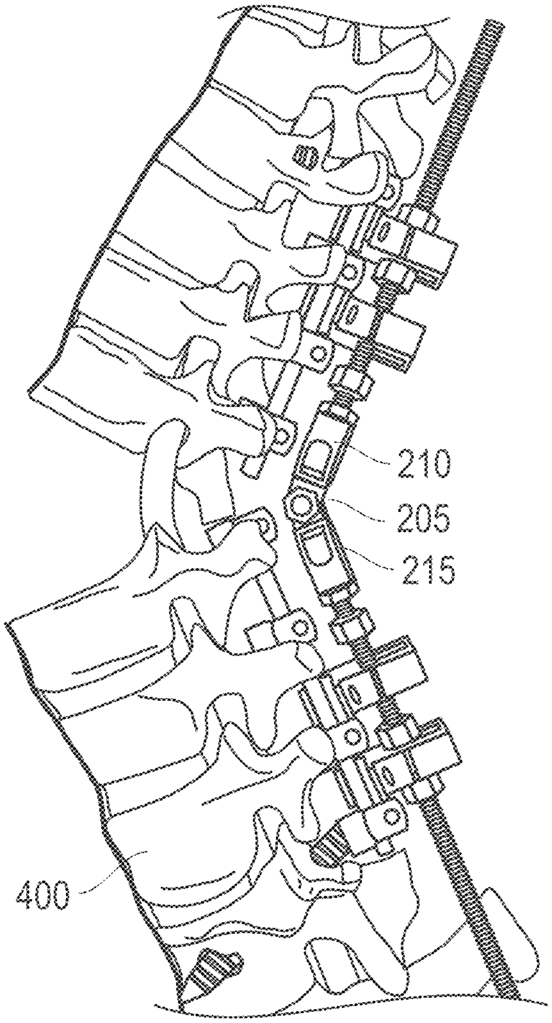
Figure 6F:
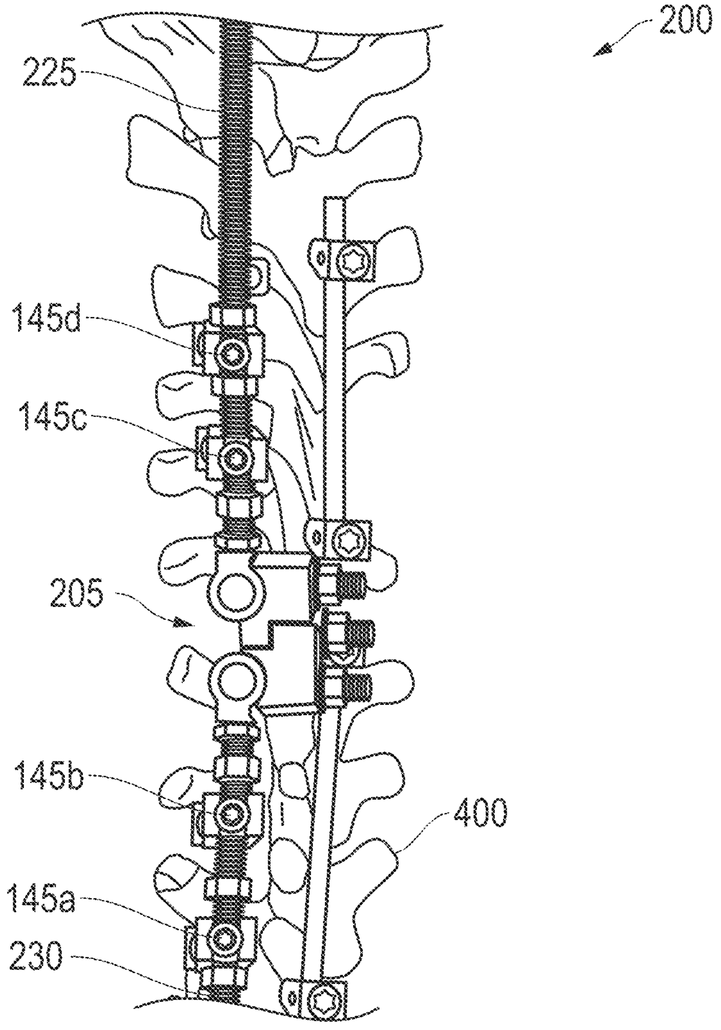
FIG. 6F illustrates a top view of the sagittal plane control correction of FIG. 6E.

FIG. 6D depicts a sagittal plane control correction using the stabilizer assembly 200. The stabilizing rods 225 and 230 are set at desired positions to position the simulated spine 400 as desired. FIG. 6E depicts a sagittal plane control correction using the stabilizer assembly 200. The stabilizer assembly 200 is rotated 90 degrees from the position shown in FIG. 6D to allow the hinge 205 to have sagittal freedom of motion. The rod-bearing leaves 210 and 215 of the hinge 205 are set at a desired angle to position the simulated spine 400 as desired. FIG. 6F depicts a top view of the sagittal plane control correction of FIG. 6E.

Figure 6G:
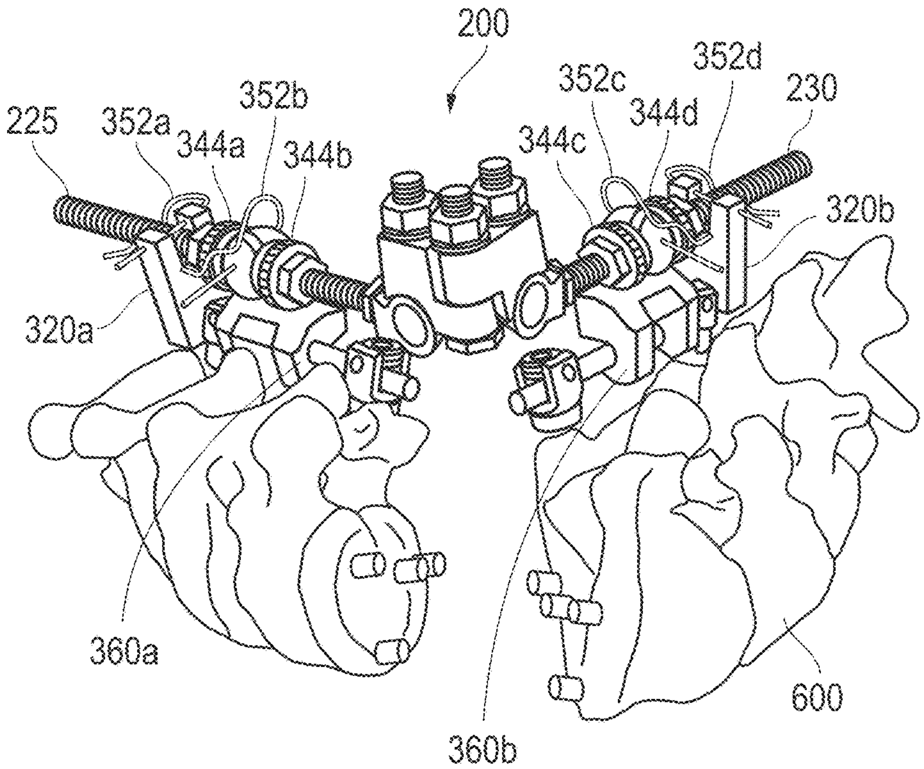
FIGS. 6G, 6H, 6I, and 6J show various views of stabilizer assembly of FIG. 2I.
Figure 6H:
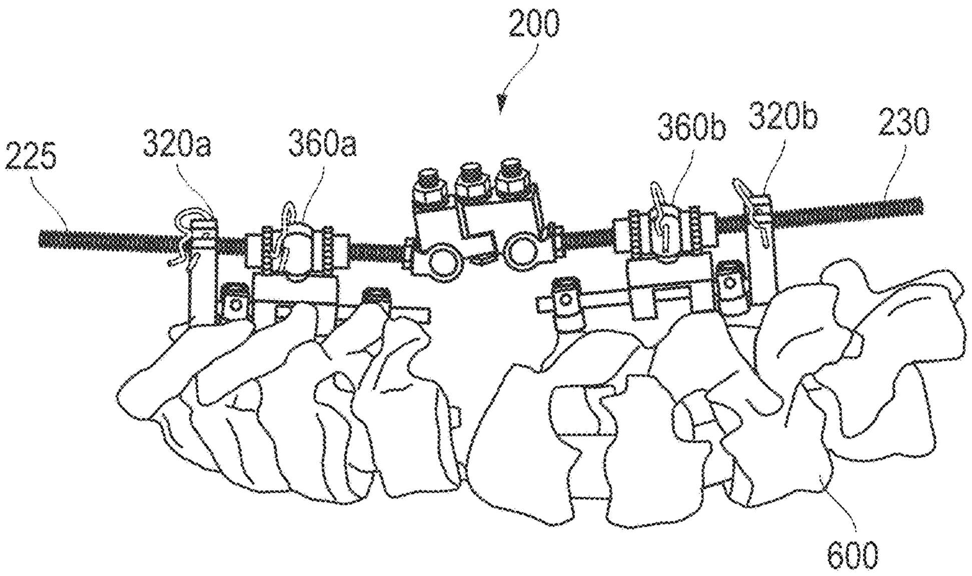
Figure 6I:
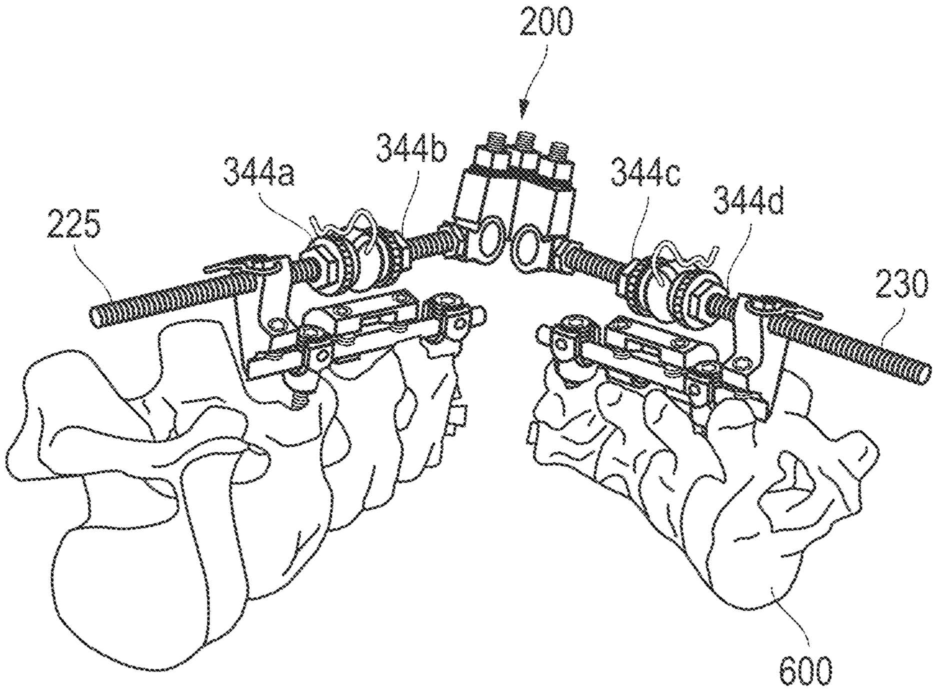
Figure 6J:
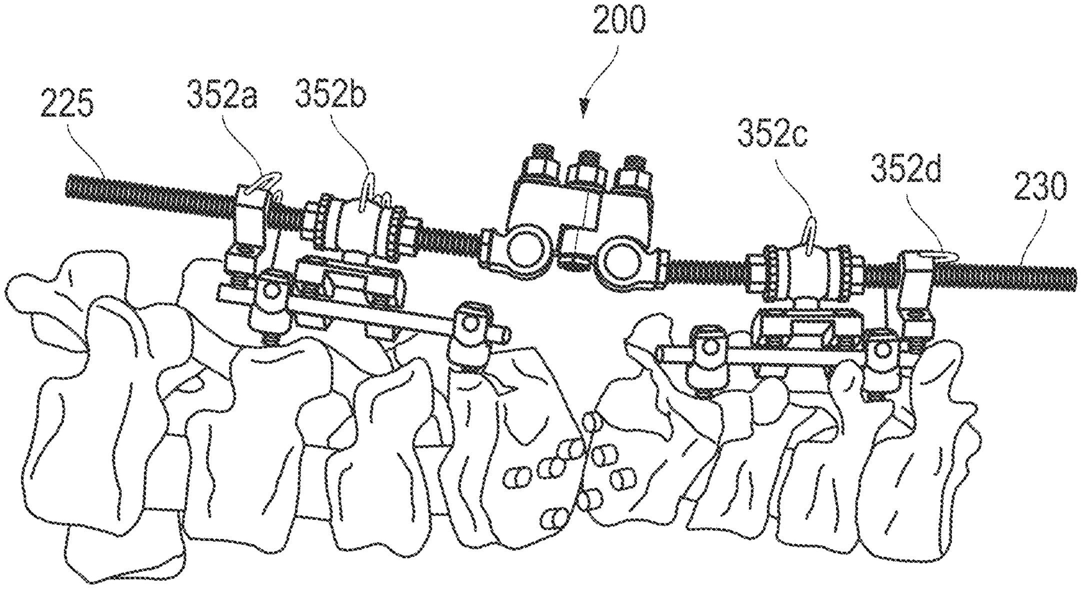

FIGS. 6G, 6H, 6I, and 6J show various views of stabilizer assembly 200 with adjustment nuts 344*a*, 344*b*, 344*c*, and 344*d* (where adjustment nuts 344*c* and 344*d* are similar to adjustment nuts 344*a* and 344*b*); retaining pins 352*a*, 352*b*, 352*c*, and 352*d*; polyaxial links 360*a* and 360*b*; and monoaxial links 320*a* and 320*b* mounted on stabilizing arms 225 and 230, with simulated spine 600. FIG. 6G indicates all of these items and illustrates the hinge 200 positioned at the apex of the spinal deformity, at which a VCR has been performed. FIG. 6H illustrates the hinge 200 positioned at the apex of the spinal deformity, at which the deformity has been corrected. FIG. 6I indicates another view (concave side view) of FIG. 6G. FIG. J indicates another view (concave side view) of FIG. 6H.

In FIGS. 6G, 6H, 6I, and 6J, adjustment nuts 344*a*, 344*b*, 344*c*, and 344*d*; polyaxial links 360*a* and 360*b*; and monoaxial links 320*a* and 320*b* include metal coated with Teflon®. All monoaxial links, polyaxial links, and adjustment nuts discussed herein may include metal, Teflon®, some combination, e.g., Teflon®-coated metal, polymers, composites, etc.

Figure 7A:
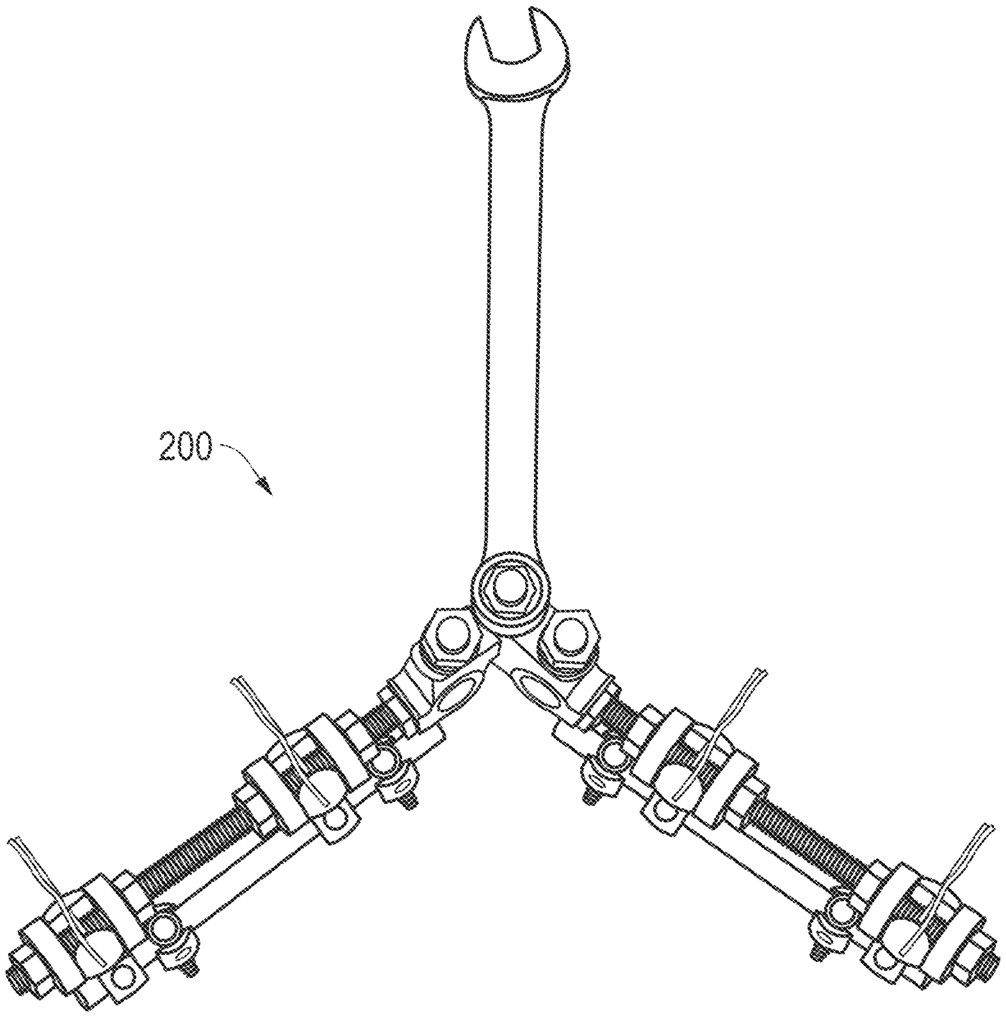
FIG. 7A shows a coronal plane control correction using the stabilizer assembly of FIG. 2I.
Figure 7B:
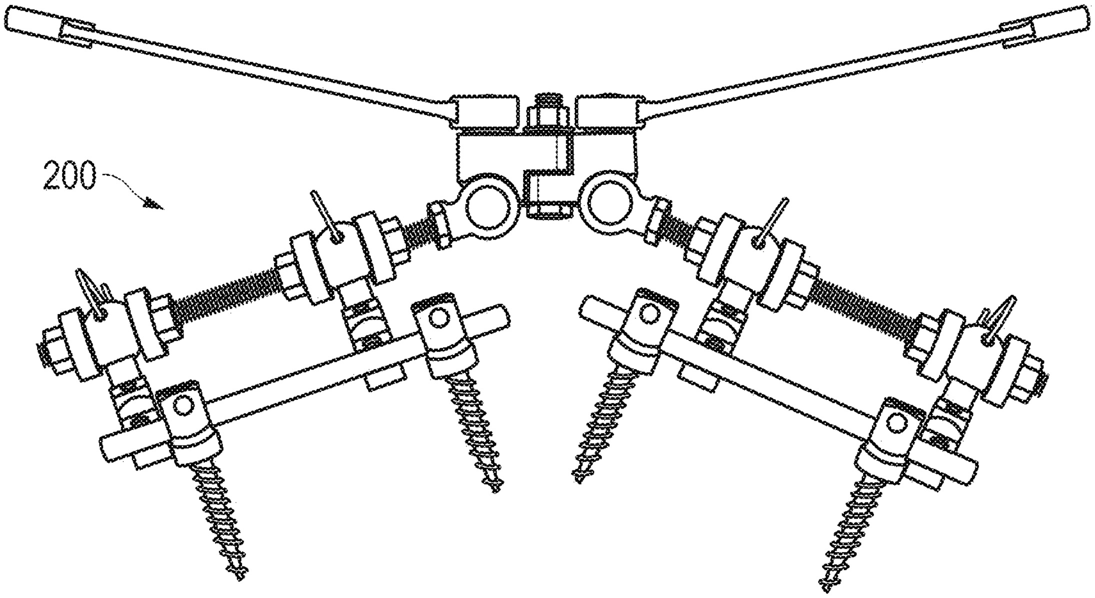
FIG. 7B shows a sagittal plane control correction using the stabilizer assembly of FIG. 2I.
Figure 7C:
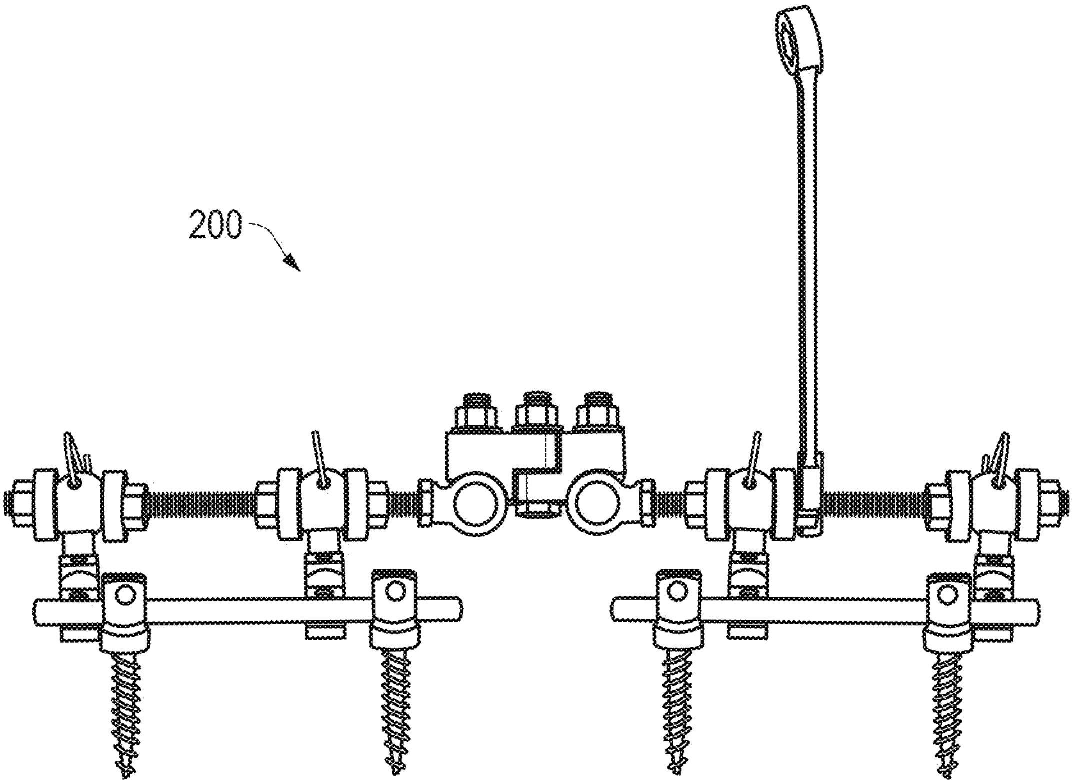
FIG. 7C shows a longitudinal correction using the stabilizer assembly of FIG. 2I.
Figure 7D:
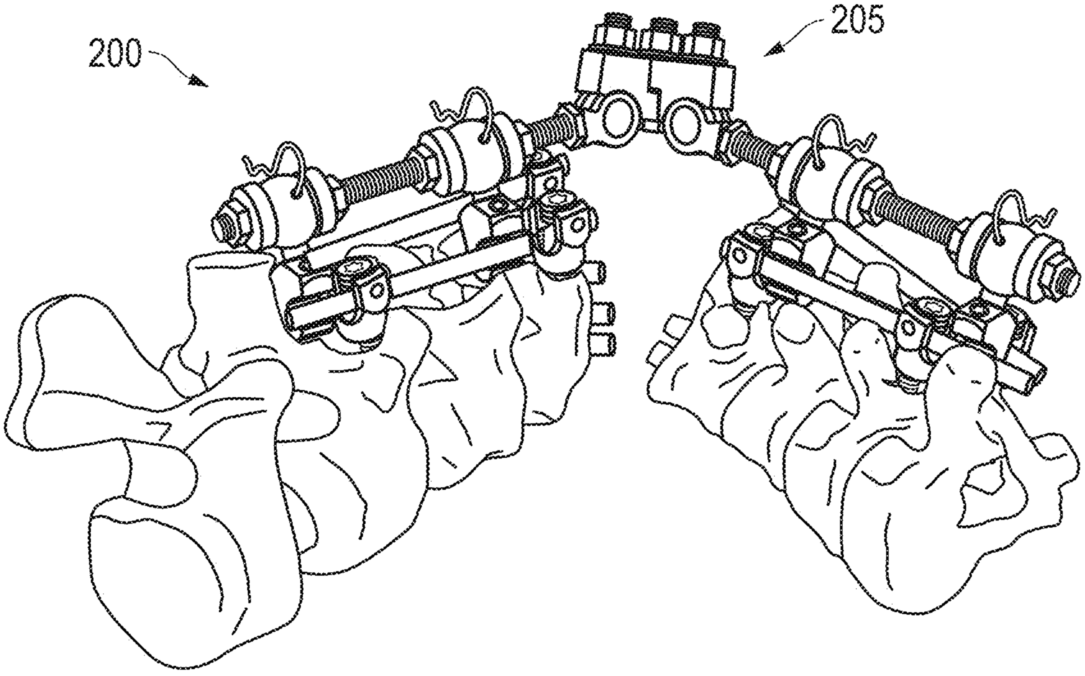
FIG. 7D shows the stabilizer assembly of FIG. 2I with the hinge positioned at the apex of a spinal deformity, at which a VCR has been performed.
Figure 7E:
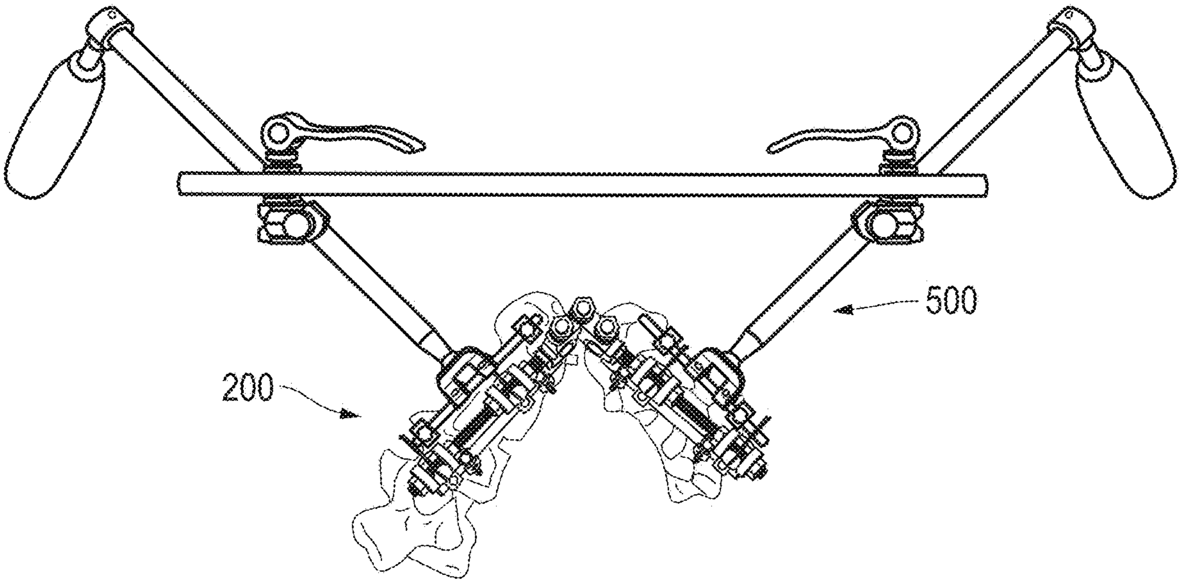
FIGS. 7E and 7F show how the hinge of the stabilizer assembly of FIG. 2I and the manipulator assembly of FIGS. 5A and 5B are used together to perform a spinal correction.
Figure 7F:
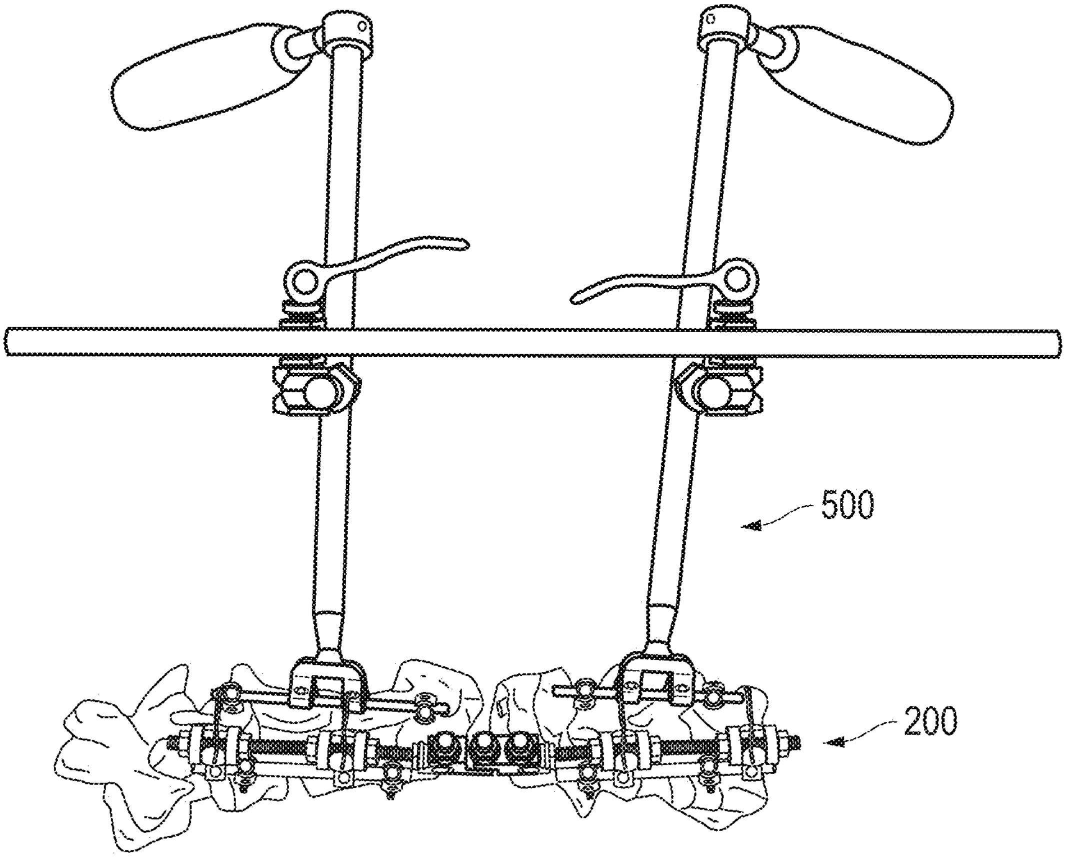
Figure 7G:
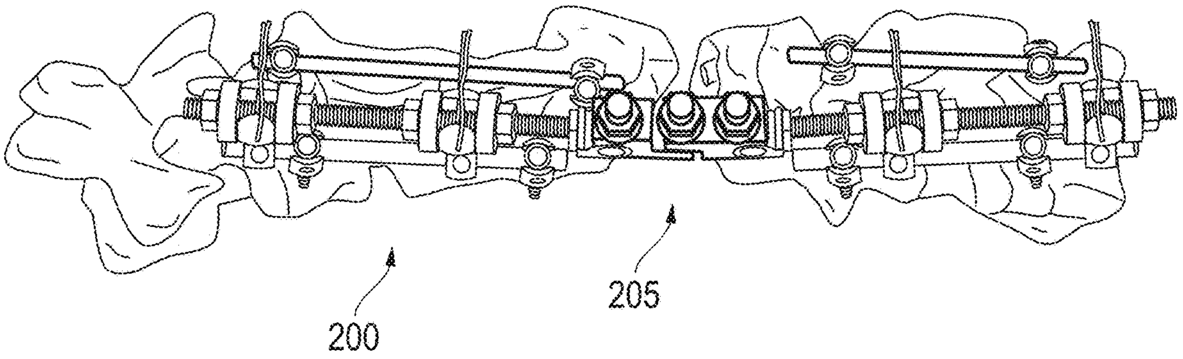
FIG. 7G shows how the hinge of the stabilizer assembly of FIG. 2I is used to stabilize the spinal correction of FIGS. 7E and 7F.

FIGS. 7A-7G illustrate various uses of the stabilizer assembly 200 of FIG. 2I. FIG. 7A shows a coronal plane control correction using the stabilizer assembly 200. FIG. 7B shows a sagittal plane control correction using the stabilizer assembly 200. FIG. 7C depicts a longitudinal correction using the stabilizer assembly 200. FIG. 7D shows the stabilizer assembly 200 with the hinge 205 positioned at the apex of a spinal deformity, at which a VCR has been performed. FIGS. 7E and 7F illustrate how the hinge of the stabilizer assembly 200 and the manipulator assembly 500 of FIGS. 5A and 5B are used together to perform a spinal correction. FIG. 7G depicts how the hinge 205 of the stabilizer assembly 200 is used to stabilize the spinal correction of FIGS. 7E and 7F.

Embodiments of the present invention can be used in conjunction with existing instruments, tools, and other devices generally used in treating spinal conditions.

Components of the present invention, including the stabilizer assembly and the polyaxial links, may be made of a non-organic material that is durable and that can be implanted in a human body, such as titanium, stainless steel, spring steel, aluminum, niobium, carbon fiber, ceramics, polymers, composites or any relatively hard material (e.g. Titanium-Aluminium-Niobium-alloy). Generally, the material selected will be biocompatible, that is, compatible with the surrounding bone and tissue.

Figure 8:
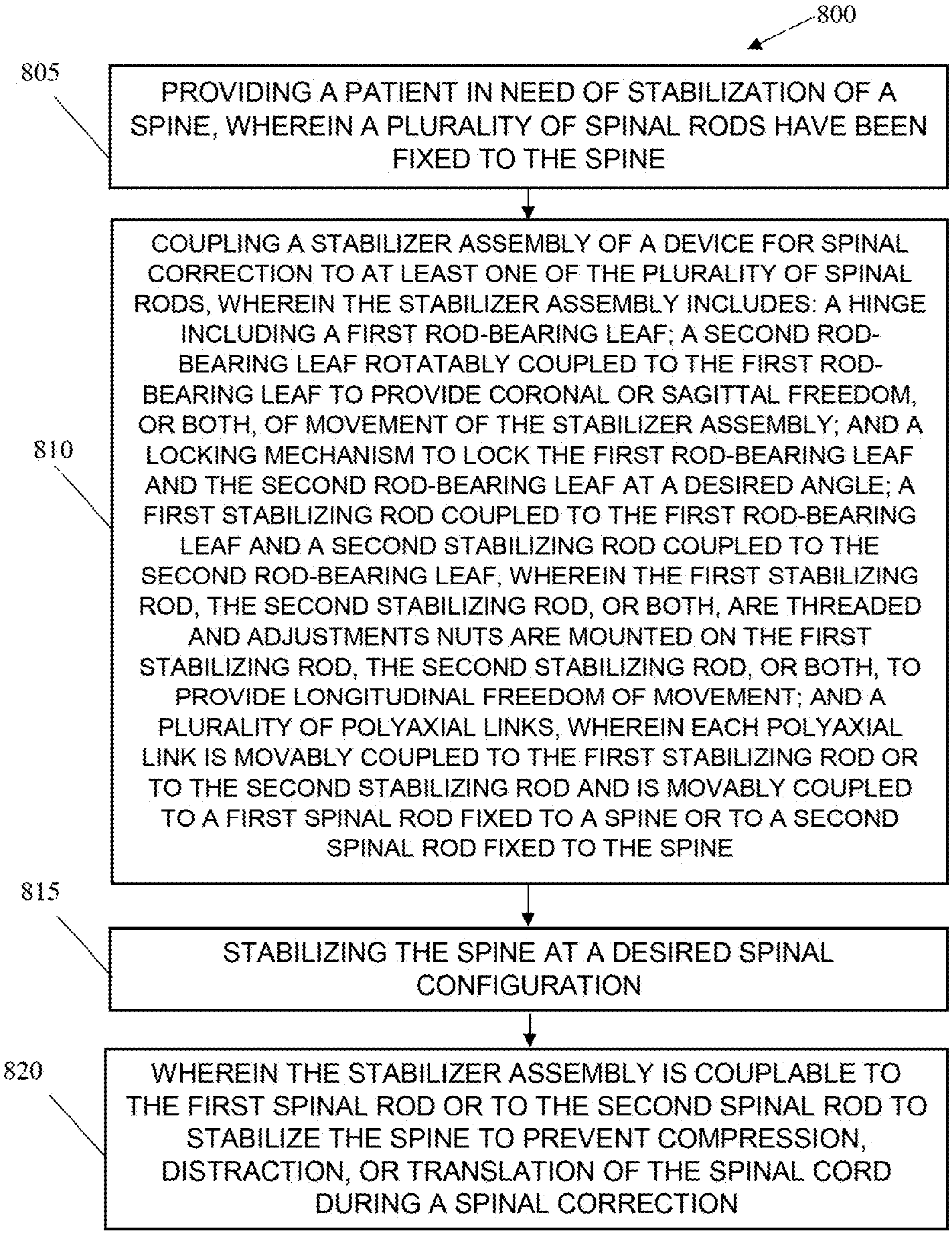
FIG. 8 depicts a flowchart of a method embodiment of the present invention.

FIG. 8 depicts a flowchart of a method embodiment of the present invention. Method 800 of stabilizing a spine includes block 805, providing a patient in need of stabilization of a spine, wherein a plurality of spinal rods have been fixed to the spine. Block 810 includes coupling a stabilizer assembly of a device for spinal correction to at least one of the plurality of spinal rods, wherein the stabilizer assembly includes a hinge including a first rod-bearing leaf; a second rod-bearing leaf rotatably coupled to the first rod-bearing leaf to provide coronal or sagittal freedom of movement, or both, of the stabilizer assembly; and a locking mechanism to lock the first rod-bearing leaf and the second rod-bearing leaf at a desired angle; a first stabilizing rod coupled to the first rod-bearing leaf and a second stabilizing rod coupled to the second rod-bearing leaf, wherein the first stabilizing rod, the second stabilizing rod, or both, are threaded and adjustment nuts are mounted on the first stabilizing rod, the second stabilizing rod, or both, to provide longitudinal freedom of movement; and a plurality of polyaxial links, wherein each polyaxial link is movably coupled to the first stabilizing rod or to the second stabilizing rod and is movably coupled to a first spinal rod fixed to a spine or to a second spinal rod fixed to the spine. Included in block 815 is fixing the spine at a desired spinal configuration. In block 820, the stabilizer assembly is couplable to the first spinal rod or to the second spinal rod to stabilize the spine to prevent compression, distraction, or translation of the spinal cord during a spinal correction.

Figure 9A:
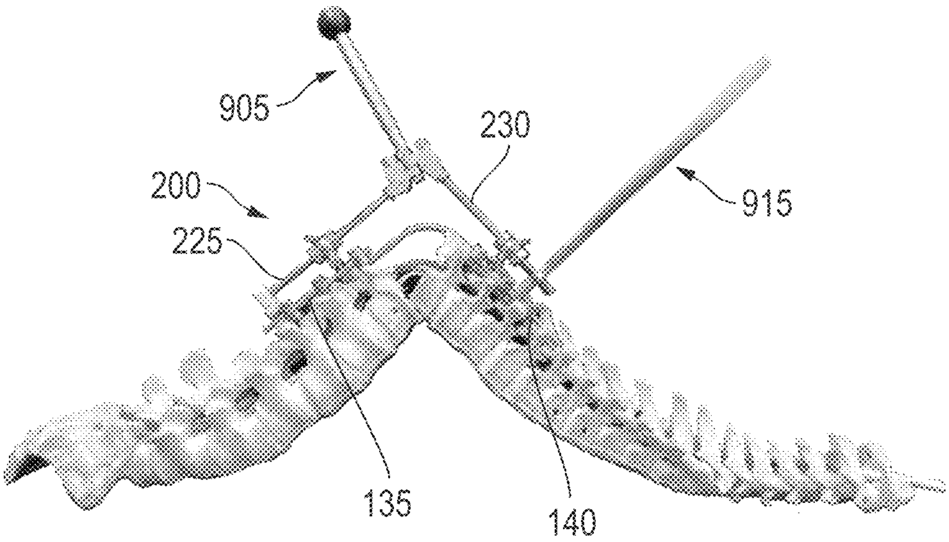
FIG. 9A shows a manipulator rod and a manipulator clamp with the stabilizer assembly.

FIG. 9A shows a manipulator rod 905 and a manipulator clamp 915 with the stabilizer assembly 200. While the manipulator rod 905 and the manipulator clamp 915 are shown and discussed in conjunction with the stabilizer assembly 200, they can be used in conjunction with other embodiments of the stabilizer assembly, such as stabilizer assembly 100 (not shown). The manipulator rod 905 is shown coupled to the hinge 205 of the stabilizer assembly 200, and the manipulator clap 915 is shown coupled to the stabilizing rod 230 of the stabilizer assembly 200 and to the spinal rod 140. The manipulator clamp 915 may also be coupled to the stabilizing rod 225 of the stabilizer assembly 200 and to the spinal rod 135.

Figure 9B:
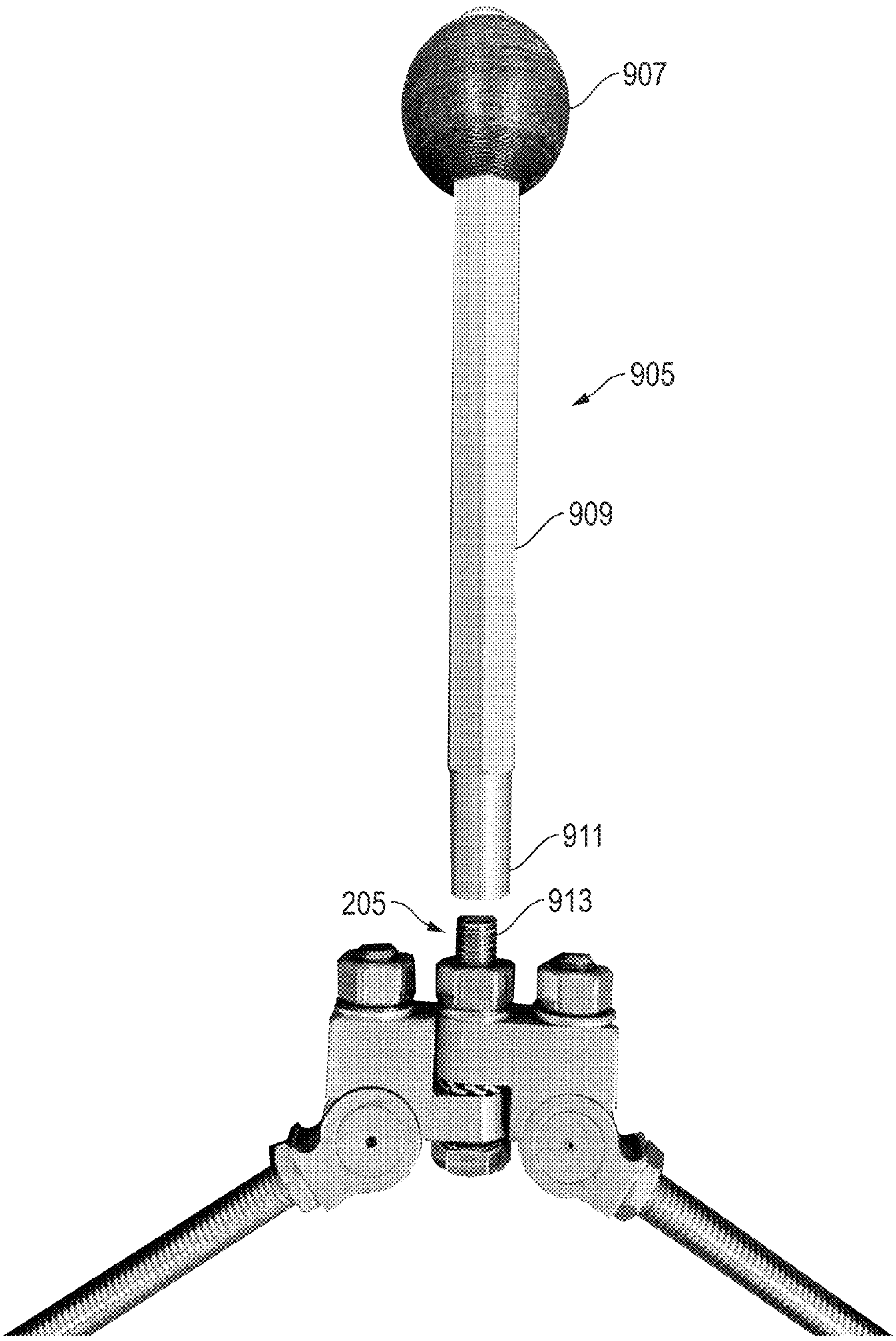
FIG. 9B shows q manipulator rod in position to be coupled to the hinge of the stabilizer assembly.

FIG. 9B shows the manipulator rod 905 in position to be coupled to the hinge 205 of the stabilizer assembly 200. The manipulator rod 905 includes a grip 907 affixed at a proximate end of the manipulator rod 905, a body 909 and a coupling mechanism 911 affixed at a distal end of the manipulator rod 905. In the exemplary embodiment shown, the coupling mechanism 911 includes a threaded recess (not shown) configured to be screwed onto a threaded hinge bolt 913. Once coupled to the hinge 205, the manipulator rod 905 can be used to manipulate the stabilizer assembly 200. The body 909 may be straight or curved may have a circular, elliptical, triangular, square, pentagonal, hexagonal, or other polygonal cross section.

Figure 9C:
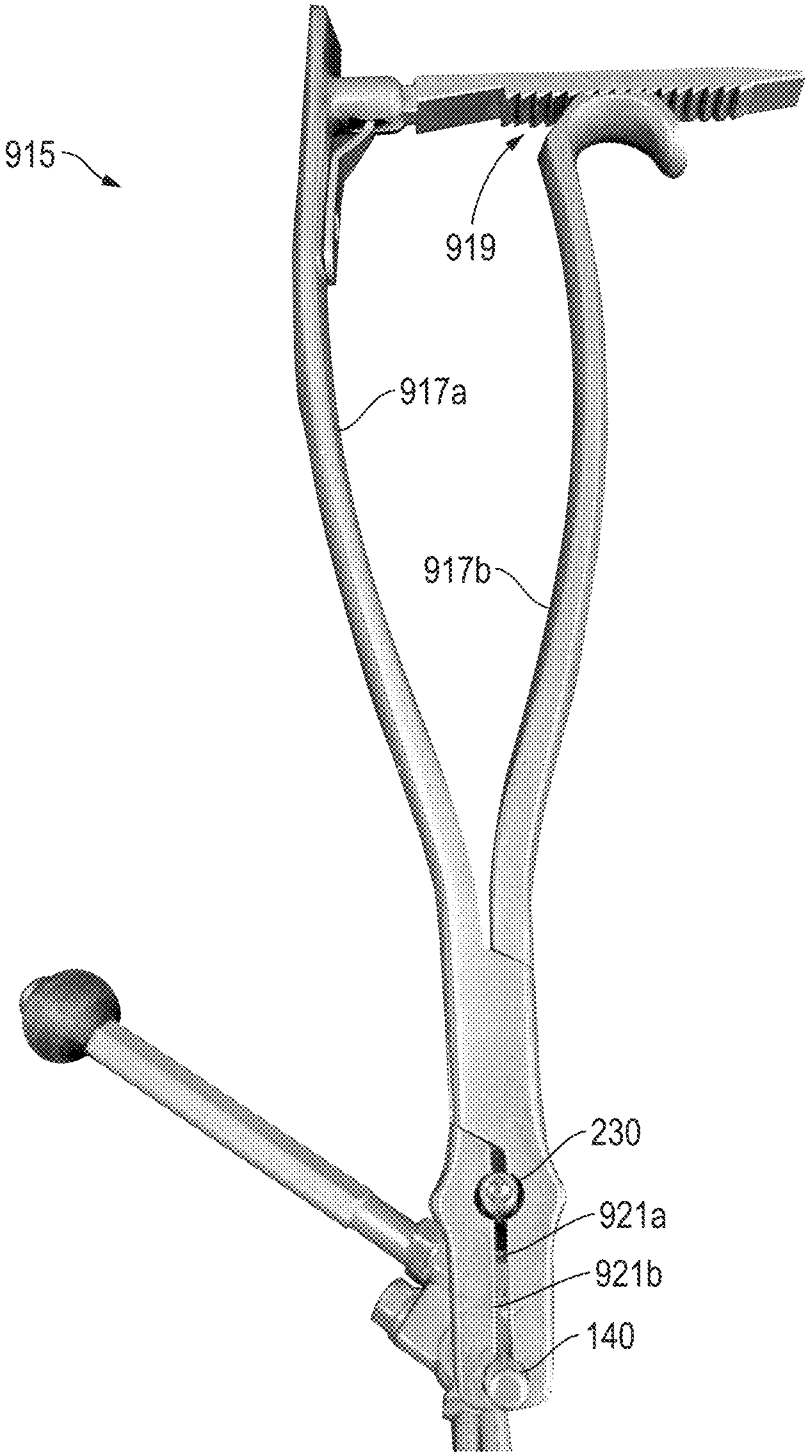
FIG. 9C shows a side view of the manipulator clamp coupled to a stabilizing rod and a spinal rod.

FIG. 9C shows a side view of the manipulator clamp 915 coupled to the stabilizing rod 230 and the spinal rod 140. The manipulator clamp 915 includes two clamp arms 917*a, b*, that are rotatably coupled together. At a proximal end of the manipulator clamp 915, the two clamp arms 917*a, b* engage each other in a disengagable ratchet mechanism 919. At a distal end of the manipulator clamp 915, each of the clamp arms 917*a, b* includes a gripping surface, gripping surfaces 921*a, b*, respectively, with recesses to engage the stabilizing rod 230 and the spinal rod 140.

Figure 9D:
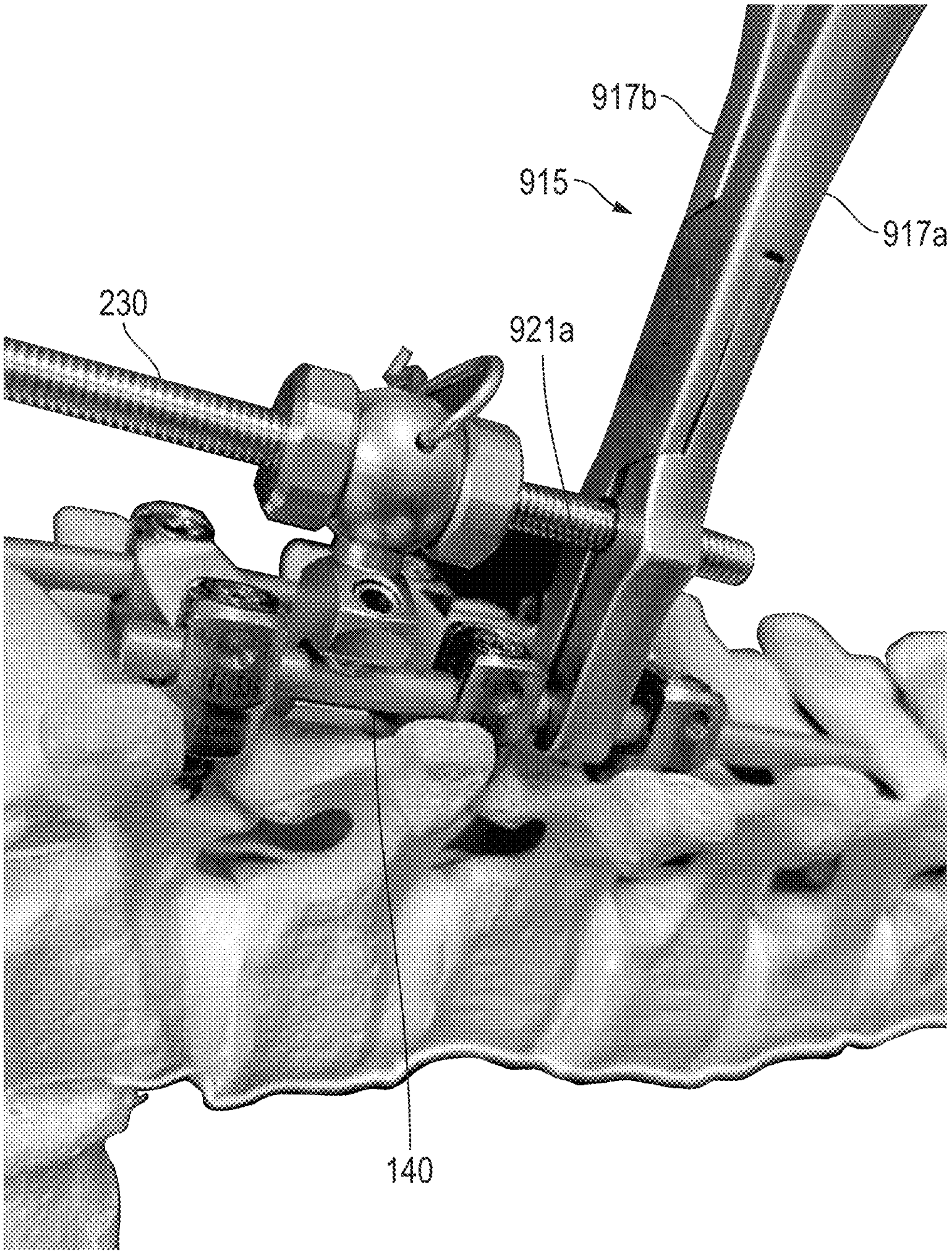
FIG. 9D shows the distal end of a manipulator clamp coupled to a stabilizing rod and a spinal rod.

FIG. 9D shows the distal end of the manipulator clamp 915 coupled to the stabilizing rod 230 and the spinal rod 140. At the distal end of the manipulator clamp 915, each of the clamp arms 917*a, b* includes a gripping surface, gripping surfaces 921*a, b*, respectively (921*b* not shown) with recesses to engage the stabilizing rod 230 and the spinal rod 140.

Figure 9E:
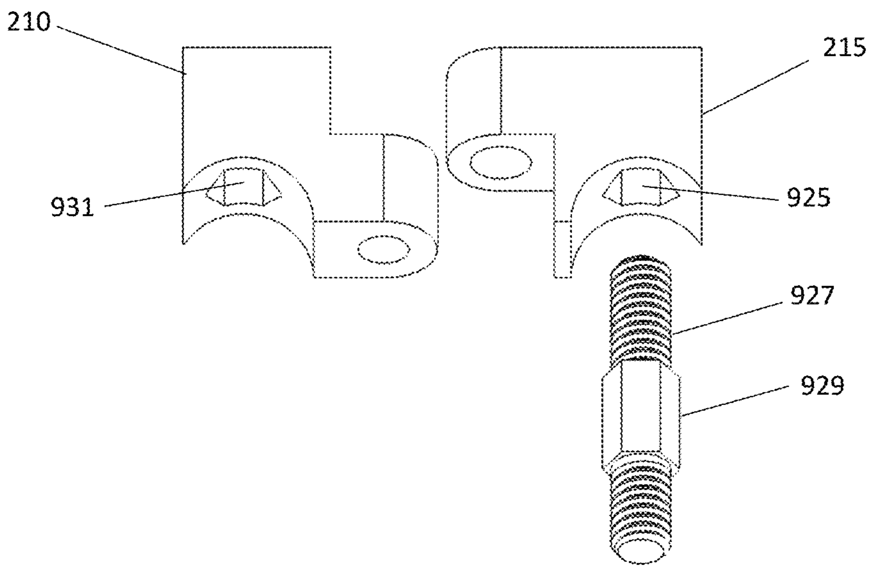
FIG. 9E shows the rod-bearing leaves of the stabilizer assembly.

FIG. 9E shows the rod-bearing leaves 210 and 215 of the stabilizer assembly 200 separately. The rod-bearing leaf 215 includes a bolt hole 925 that is configured to receive a bolt 927 bearing a nut 929 such that the bolt 927 is retained by the rod-bearing leaf 210. The bolt 927 couples the stabilizing rod 230 to the rod-bearing leaf 215. Similarly, rod-bearing leaf 210 includes a bolt hole 931 that is configured to receive a bolt (not shown) bearing a nut (not shown) such that the bolt is retained by the rod-bearing leaf 210 to couple a stabilizing rod 225 (not shown) to the rod-bearing leaf 210.

Figure 9F:
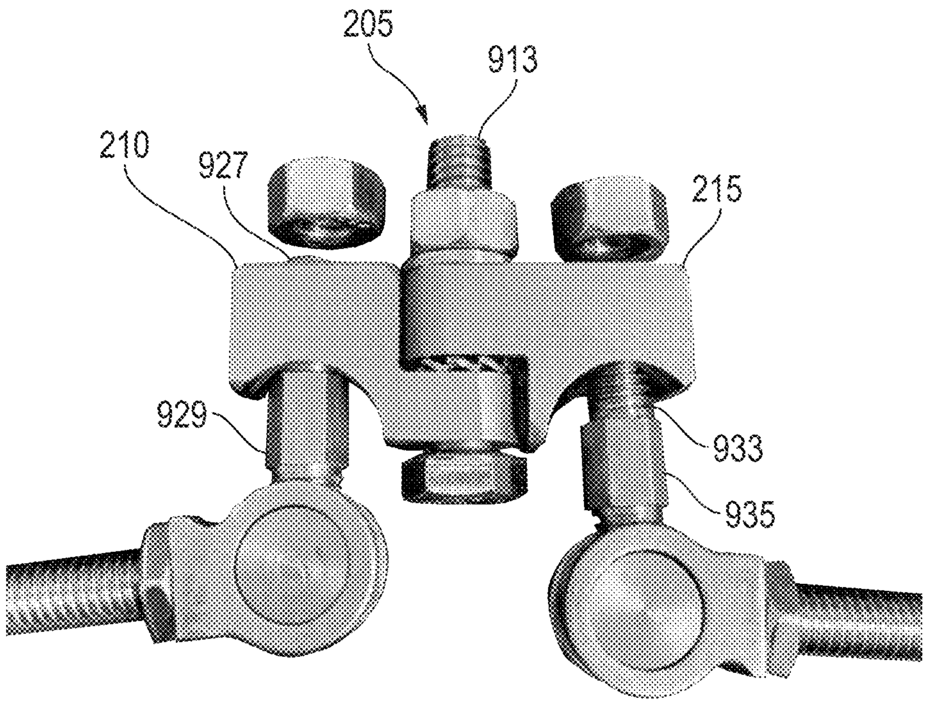
FIG. 9F shows the rod-bearing leaves of the stabilizer assembly coupled at the hinge.

FIG. 9F shows the rod-bearing leaves 210 and 215 of the stabilizer assembly 200 coupled at the hinge 205. In FIG. 9F, the rod-bearing leaves 210 and 215 are shown coupled by the hinge bolt 913, with bolts 927 and 933, bearing nuts 929 and 935, respectively, partially inserted into the bolt holes 925 and 931 (not shown), respectively.

One skilled in the art of medical treatment of human hip ailments will recognize that the device for treating spinal maladies including stabilizer assembly 100, stabilizer assembly 200, and method 700 provide effective methods and systems that reduce risk for compression, distraction, or translation of the spinal cord during stabilization, manipulation, and fixation of a deformed spine subject to a vertebral column resection surgery or a spinal correction.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of" As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step, or a limitation) or group of integers (e.g., feature(s), element(s), characteristic(s), property(ies), method/process(s) steps, or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the devices and/or methods disclosed and claimed herein can be made and executed without undue experimentation in light of the present disclosure. While the devices and/or methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope, and concept of the invention as defined by the appended claims.

Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

To aid the Patent Office, and any readers of any patent issued on this application in interpreting the claims appended hereto, applicants wish to note that they do not intend any of the appended claims to invoke 35 U.S.C. § 112(f) as it exists on the date of filing hereof unless the words "means for" or "step for" are explicitly used in the particular claim.

What is claimed is:

1. A manipulator rod for use with a device for spinal correction, the manipulator rod comprising:
- a grip at a proximate end of the manipulator rod;
- a body affixed to the grip, wherein the body is straight or curved and wherein the body has a circular, elliptical, triangular, square, pentagonal, hexagonal, or other polygonal cross section; and
- a coupling mechanism affixed to the body at a distal end of the manipulator rod;
- wherein the manipulator rod is configured to be coupled to a hinge of the device for spinal correction, wherein the device for spinal correction comprises:
  - a stabilizer assembly comprising:
  - the hinge comprising:
    - a first rod-bearing leaf, wherein the first rod-bearing leaf is flat;
    - a second rod-bearing leaf rotatably coupled to the first rod-bearing leaf to provide coronal or sagittal freedom of movement, or both, of the stabilizer assembly, wherein the second rod-bearing leaf is flat;
    - a locking mechanism to lock the first rod-bearing leaf and the second rod-bearing leaf at a desired angle;
  - a first stabilizing rod coupled to the first rod-bearing leaf; and
  - a second stabilizing rod coupled to the second rod-bearing leaf; and
  - wherein the stabilizer assembly is couplable to a first spinal rod fixed to a spine or to a second spinal rod fixed to the spine to stabilize the spine to prevent compression, distraction, or translation of the spinal cord during a spinal correction.

2. The manipulator rod of claim 1, wherein the coupling mechanism comprises a threaded recess configured to receive a threaded bolt.

3. A kit comprising:
- a manipulator rod for use with a device for spinal correction, the manipulator rod comprising:
  - a grip at a proximate end of the manipulator rod;
  - a body affixed to the grip, wherein the body is curved and wherein the body of the manipulator rod has a circular, elliptical, triangular, square, pentagonal, hexagonal, or other polygonal cross section; and
  - a coupling mechanism affixed to the body at a distal end of the manipulator rod;
  - wherein the manipulator rod is configured to be coupled to a hinge of the device for spinal correction; and
- the device for spinal correction comprising:
  - a stabilizer assembly comprising:
  - the hinge, comprising:
  - a first rod-bearing leaf, wherein the first rod-bearing leaf is flat;
  - a second rod-bearing leaf rotatably coupled to the first rod-bearing leaf to provide coronal or sagittal freedom of movement, or both, of the stabilizer assembly, wherein the second rod-bearing leaf is flat;
  - a locking mechanism to lock the first rod-bearing leaf and the second rod-bearing leaf at a desired angle;
  - a first stabilizing rod coupled to the first rod-bearing leaf; and
  - a second stabilizing rod coupled to the second rod-bearing leaf; and
  - wherein the stabilizer assembly is couplable to a first spinal rod fixed to a spine or to a second spinal rod fixed to the spine to stabilize the spine to prevent compression, distraction, or translation of the spinal cord during a spinal correction.

4. The kit of claim 3, wherein the body of the manipulator rod has a circular, elliptical, triangular, square, pentagonal, hexagonal, or other polygonal cross section.

5. A manipulator clamp for use with a device for spinal correction, the manipulator clamp comprising:
- two clamp arms rotatably coupled together, wherein the two clamp arms engage each other in a disengageable ratchet mechanism at a proximate end of the manipulator clamp, and wherein each clamp arm comprises a gripping surface at a distal end of the manipulator clamp;

wherein the manipulator clamp is configured to engage a stabilizing rod of a device for spinal correction and a spinal rod, wherein the device for spinal correction comprises:

a stabilizer assembly comprising:

a hinge comprising:

a first rod-bearing leaf, wherein the first rod-bearing leaf is flat;

a second rod-bearing leaf rotatably coupled to the first rod-bearing leaf to provide coronal or sagittal freedom of movement, or both, of the stabilizer assembly, wherein the second rod-bearing leaf is flat;

a locking mechanism to lock the first rod-bearing leaf and the second rod-bearing leaf at a desired angle;

a first stabilizing rod coupled to the first rod-bearing leaf; and a second stabilizing rod coupled to the second rod-bearing leaf; and wherein the stabilizer assembly is couplable to a first spinal rod fixed to a spine or to a second spinal rod fixed to the spine to stabilize the spine to prevent compression, distraction, or translation of the spinal cord during a spinal correction.

6. The manipulator clamp of claim 5, wherein the gripping surface of each clamp arm comprises a first recess to engage the first or second stabilizing rod and a second recess to engage the first or second spinal rod.

7. A kit comprising:

a manipulator clamp for use with a device for spinal correction, the manipulator clamp comprising:

two clamp arms rotatably coupled together, wherein the two clamp arms engage each other in a disengageable ratchet mechanism at a proximate end of the manipulator clamp, and wherein each clamp arm comprises a gripping surface at a distal end of the manipulator clamp;

wherein the manipulator clamp is configured to engage a stabilizing rod of a device for spinal correction and a spinal rod; and the device for spinal correction, comprising:

a stabilizer assembly comprising:

a hinge comprising:

a first rod-bearing leaf, wherein the first rod-bearing leaf is flat;

a second rod-bearing leaf rotatably coupled to the first rod-bearing leaf to provide coronal or sagittal freedom of movement, or both, of the stabilizer assembly, wherein the second rod-bearing leaf is flat;

a locking mechanism to lock the first rod-bearing leaf and the second rod-bearing leaf at a desired angle;

a first stabilizing rod coupled to the first rod-bearing leaf; and a second stabilizing rod coupled to the second rod-bearing leaf; and wherein the stabilizer assembly is couplable to a first spinal rod fixed to a spine or to a second spinal rod fixed to the spine to stabilize the spine to prevent compression, distraction, or translation of the spinal cord during a spinal correction.

8. The kit of claim 7, wherein the gripping surface of each clamp arm of the manipulator clamp comprises a first recess to engage the first or second stabilizing rod and a second recess to engage the first or second spinal rod.

9. A device for spinal correction comprising:

a stabilizer assembly comprising:

a hinge comprising:

a first rod-bearing leaf, wherein the first rod-bearing leaf is flat;

a second rod-bearing leaf rotatably coupled to the first rod-bearing leaf to provide coronal or sagittal freedom of movement, or both, of the stabilizer assembly, wherein the second rod-bearing leaf is flat;

a locking mechanism to lock the first rod-bearing leaf and the second rod-bearing leaf at a desired angle;

a first stabilizing rod coupled to the first rod-bearing leaf;

a second stabilizing rod coupled to the second rod-bearing leaf;

wherein the first rod-bearing leaf comprises a first bolt hole configured to receive a second nut-bearing bolt to couple the first stabilizing rod to the first rod-bearing leaf, and wherein the second rod-bearing leaf comprises a second bolt hole configured to receive a second nut-bearing bolt to couple the second stabilizing rod to the second rod-bearing leaf; and wherein the stabilizer assembly is couplable to a first spinal rod fixed to the spine or to a second spinal rod fixed to the spine to stabilize the spine to prevent compression, distraction, or translation of the spinal cord during a spinal correction.

* * * * *